US009199958B2

(12) United States Patent
Janka et al.

(10) Patent No.: US 9,199,958 B2
(45) Date of Patent: *Dec. 1, 2015

(54) OXIDATION PROCESS TO PRODUCE A CRUDE AND/OR PURIFIED CARBOXYLIC ACID PRODUCT

(71) Applicant: Eastman Chemical Company, Kingsport, TN (US)

(72) Inventors: Mesfin Ejerssa Janka, Kingsport, TN (US); David Lange, Blountville, TN (US); Michael C. Morrow, Kingsport, TN (US); Bradford Russell Bowers, Chuckey, TN (US); Kenny Randolph Parker, Afton, TN (US); Ashfaq Shaikh, Kingsport, TN (US); Lee Reynolds Partin, Kingsport, TN (US); Charles Sumner, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/525,624

(22) Filed: Oct. 28, 2014

(65) Prior Publication Data
US 2015/0051412 A1 Feb. 19, 2015

Related U.S. Application Data

(63) Continuation-in-part of application No. 13/228,816, filed on Sep. 9, 2011, now abandoned.

(60) Provisional application No. 61/489,496, filed on May 24, 2011.

(51) Int. Cl.
*C07D 307/68* (2006.01)

(52) U.S. Cl.
CPC .................................. *C07D 307/68* (2013.01)

(58) Field of Classification Search
CPC .................................................... C07D 307/68
USPC ......................................................... 549/485
See application file for complete search history.

(56) References Cited

U.S. PATENT DOCUMENTS

| 2,797,197 | A | 6/1957 | Thompson et al. |
|---|---|---|---|
| 3,203,963 | A | 8/1965 | Hales et al. |
| 3,326,944 | A | 6/1967 | Lew |
| 4,977,283 | A | 12/1990 | Leupold et al. |
| 6,737,481 | B1 | 5/2004 | Kurian et al. |
| 7,052,764 | B2 | 5/2006 | Chang et al. |
| 7,385,081 | B1 | 6/2008 | Gong |
| 7,411,078 | B2 | 8/2008 | Miura et al. |
| 7,572,925 | B2 | 8/2009 | Dumesic et al. |
| 7,700,788 | B2 | 4/2010 | Lilga et al. |
| 8,183,020 | B2 | 5/2012 | Hanke |
| 8,193,381 | B2 | 6/2012 | Lilga et al. |
| 8,193,382 | B2 | 6/2012 | Lilga et al. |
| 8,748,479 | B2 | 6/2014 | Shaikh et al. |
| 8,772,513 | B2 | 7/2014 | Janka et al. |
| 8,791,277 | B2 | 7/2014 | Janka et al. |
| 8,791,278 | B2 | 7/2014 | Shaikh et al. |
| 8,796,477 | B2 | 8/2014 | Janka et al. |
| 8,809,556 | B2 | 8/2014 | Janka et al. |
| 8,846,960 | B2 | 9/2014 | Janka et al. |
| 8,916,719 | B2 | 12/2014 | Shaikh et al. |
| 8,916,720 | B2 | 12/2014 | Shaikh et al. |
| 8,969,404 | B2 | 3/2015 | Janka et al. |
| 2003/0055271 | A1 | 3/2003 | Grushin et al. |
| 2006/0205977 | A1 | 9/2006 | Sumner, Jr. et al. |
| 2007/0232815 | A1 | 10/2007 | Miura et al. |
| 2009/0124829 | A1 | 5/2009 | Gong |
| 2009/0131690 | A1 | 5/2009 | Gruter et al. |
| 2009/0156841 | A1 | 6/2009 | Sanborn et al. |
| 2009/0326262 | A1 | 12/2009 | Wan |
| 2010/0210867 | A1 | 8/2010 | Bustamante et al. |
| 2011/0092720 | A1 | 4/2011 | Yutaka et al. |
| 2012/0302768 | A1 | 11/2012 | Janka et al. |
| 2012/0302769 | A1 | 11/2012 | Janka et al. |
| 2012/0302770 | A1 | 11/2012 | Janka et al. |
| 2012/0302771 | A1 | 11/2012 | Janka et al. |
| 2012/0302772 | A1 | 11/2012 | Shaikh et al. |
| 2012/0302773 | A1 | 11/2012 | Janka et al. |
| 2013/0345452 | A1 | 12/2013 | Janka et al. |
| 2014/0024844 | A1 | 1/2014 | Janka et al. |

(Continued)

FOREIGN PATENT DOCUMENTS

| CS | 87340 | 7/1959 |
|---|---|---|
| EP | 1 834 951 A1 | 9/2007 |

(Continued)

OTHER PUBLICATIONS

Slavinskaya, V. A., et al., "Liquid-Phase Catalytic Oxidation of 5-Methylfurfural," React. Kinet. Catal. Lett., 1979, vol. 11, No. 3, pp. 215-220.

Gandini, A., et al., "Rapid Communication: The Furan Counterpart of Poly(ethylene terephthalate): An Alternative Material Based on Renewable Resources," Journal of Polymer Science: Part A: Polymer Chemistry, 2009, vol. 47, pp. 295-298, Wiley Periodicals, Inc.

Partenheimer, W. et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts," Adv. Synth. Catal., 2001, vol. 343, No. 1, pp. 102-111.

Lewkowski, J.; "Synthesis, Chemistry and Applications of 5-Hydroxymethylfurfural and its Derivatives," ARKIVOC, 2001, pp. 17-54.

Zakharov, I. V., "Mechanism of Initiation and Inhibition by Mn(II) in Hydrocarbon Oxidation in the Presence a Cobalt-Manganese Bromide Catalyst," Kinetics and Catalysis, 1998, vol. 39, No. 4, pp. 485-492.

(Continued)

Primary Examiner — Taofiq A Solola
(74) Attorney, Agent, or Firm — Phan Law Group PLLC

(57) ABSTRACT

Disclosed is an oxidation process to produce a crude carboxylic acid product carboxylic acid product. The process comprises oxidizing a feed stream comprising at least one oxidizable compound to generate a crude carboxylic acid slurry comprising furan-2,5-dicarboxylic acid (FDCA) and compositions thereof. Also disclosed is a process to produce a dry purified carboxylic acid product by utilizing various purification methods on the crude carboxylic acid.

11 Claims, 6 Drawing Sheets

(56) References Cited

U.S. PATENT DOCUMENTS

| | | | |
|---|---|---|---|
| 2014/0142328 A1 | 5/2014 | Shaikh et al. | |
| 2014/0235880 A1 | 8/2014 | Shaikh et al. | |
| 2014/0364633 A1 | 12/2014 | Janka et al. | |

FOREIGN PATENT DOCUMENTS

| | | |
|---|---|---|
| EP | 2 197 868 B1 | 4/2011 |
| EP | 2 197 865 B1 | 8/2012 |
| GB | 934 292 A | 8/1963 |
| JP | 2007-261986 A | 10/2007 |
| JP | 2007-261990 A | 10/2007 |
| JP | 2009-001519 A | 1/2009 |
| JP | 2009-013079 A | 1/2009 |
| JP | 2009-242312 A | 10/2009 |
| SU | 162962 A | 9/1962 |
| WO | 01/72732 A2 | 10/2001 |
| WO | WO 02/098836 A1 | 12/2002 |
| WO | WO 2007/092183 A2 | 8/2007 |
| WO | WO 2008/054804 A2 | 5/2008 |
| WO | WO 2009/023174 A2 | 2/2009 |
| WO | WO 2009/030506 A4 | 3/2009 |
| WO | WO 2009/030507 A4 | 3/2009 |
| WO | WO 2010/077133 A1 | 7/2010 |
| WO | WO 2010/132740 A2 | 11/2010 |
| WO | WO 2011/043660 A2 | 4/2011 |
| WO | 2012/161970 A2 | 11/2012 |
| WO | WO 2012/161968 A1 | 11/2012 |
| WO | WO 2014/193634 A1 | 12/2014 |
| WO | WO 2014/197195 A2 | 12/2014 |

OTHER PUBLICATIONS

Jiao, X. J. et al., "Kinetics of Manganese(III) Acetate in Acetic Acid: Generation of Mn(III) with Co(III), Ce(IV), and Dibromide Radicals; Reactions of Mn(III) with Mn(II), Co(II), Hydrogen Bromide, and Alkali Bromides," Inorg. Chem., 2000, vol. 39, pp. 1549-1554, American Chemical Society.

PCT International Search Report and Written Opinion dated Jul. 27, 2012 for International Application No. PCT/US2012/037223.

PCT International Search Report and Written Opinion dated Aug. 7, 2012 for International Application No. PCT/US2012/037218.

PCT International Search Report and Written Opinion dated Jul. 27, 2012 for International Application No. PCT/US2012/037204.

PCT International Search Report and Written Opinion dated Jul. 27, 2012 for International Application No. PCT/US2012/037206.

PCT International Search Report and Written Opinion dated Aug. 3, 2012 for International Application No. PCT/US2012/037210.

PCT International Search Report and Written Opinion dated Aug. 23, 2012 for International Application No. PCT/US2012/037228.

Chheda et al., "Production of 5-hydromethylfurfural and furfural by dehydration of biomass-derived mono- and poly-saccharides." Green Chemistry, vol. 9, pp. 342-350 (2007).

Werpy et al., "Top Value Added Chemicals from Biomass" DOE (Pacific NW National Laboratory) (Aug. 2004).

Verevkin et al., "Biomass-Derived Platform Chemicals: Thermodynamic Studies on the Conversion of 5-Hydroxymethylfurfural into Bulk Intermediates" Ind. Eng. Chem. Res., vol. 48, pp. 10087-10093 (2009).

Manasek, Z., "Modification of a Fiber-Forming Polyester Based on 2,5-Furandicarboxylic Acid", Mar. 20, 1963, pp. 35-38, UDC 677. 465.

Rodivilova et al., "Synthesis and Investigation of Polyarylates Based on 2,5-Furandicarboxylic Acid and Diphenylolpropane", Khimiya I Khimicheskaya Tekhnologiya, No. 7, 1968, pp. 818-821.

Office Action dated Jun. 6, 2013 received in co-pending U.S. Appl. No. 13/228,816 (Now Abandoned).

PCT International Search Report and Written Opinion dated Jul. 29, 2013 for International Application No. PCT/US2013/044935.

PCT International Search Report and Written Opinion dated Aug. 9, 2013 for International Application No. PCT/US2013/044932.

Office Action dated Sep. 30, 2013 received in co-pending U.S. Appl. No. 13/758,080.

Moldenhauer, et al., "Beitrage zur Furanchemie I", Justus Liebigs Annalen Der Chemie, vol. 580, 1953, pp. 169-190.

Office Action dated Oct. 25, 2013 received in co-pending U.S. Appl. No. 13/228,813.

PCT International Search Report and Written Opinion dated Oct. 31, 2013 for International Application No. PCT/US2013/050799.

PCT International Search Report and Written Opinion dated Nov. 28, 2013 for International Application No. PCT/US2013/050794.

PCT International Search Report and Written Opinion dated Dec. 30, 2013 for International Application No. PCT/US2013/056362.

Office Action date Apr. 17, 2014 received in co-pending U.S. Appl. No. 13/758,072.

Copending U.S. Appl. No. 14/282,360, filed May 20, 2014, Janka et al.

Office Action dated May 29, 2014 received in co-pending U.S. Appl. No. 13/228,816.

Copending U.S. Appl. No. 14/317,588, filed Jun. 27, 2014, Parker et al.

Copending U.S. Appl. No. 14/317,692, filed Jun. 27, 2014, Janka et al.

Copending U.S. Appl. No. 14/317,782, filed Jun. 27, 2014, Parker et al.

Copending U.S. Appl. No. 14/317,875, filed Jun. 27, 2014, Janka et al.

Office Action dated Sep. 26, 2014, received in co-pending U.S. Appl. No. 13/758,072.

Notice of Allowance dated Dec. 17, 2014 received in co-pending U.S. Appl. No. 13/758,080.

M. Kroeger et al., "A new approach for the production of 2,5-furandicarboxylic acid by in situ oxidation of 5-hydroxymethylfurfural starting from fructose", Topics in Catalysis, Baltzer Science Publishers, Bussum, NL, vol. 13, Jan. 1, 2000, pp. 237-242.

J. Kiss et al., "18. Uber Muscarin. 11 Mitteilung Synthese von bisquaternaren, dem Muscarin ahnlichen Verbindungen", Helvetica Chimica Acta, vol. 44, No. 1, Jan. 1, 1961, pp. 141-147.

Extended European Search Report issued in EP Application No. 12 789 055.6 dated Oct. 23, 2014.

OXIDATION PROCESS TO PRODUCE A CRUDE AND/OR PURIFIED CARBOXYLIC ACID PRODUCT

CROSS REFERENCE TO RELATED APPLICATIONS

This application is a continuation-in-part of U.S. Non-Provisional application Ser. No. 13/228,816 filed Sep. 9, 2011 which claims priority to U.S. Provisional Application Ser. No. 61/489,496 filed May 24, 2011, now expired, the disclosures of which are herein incorporated by reference in their entirety to the extent they do not contradict the statements herein.

FIELD OF THE INVENTION

The present invention relates to a process to produce a carboxylic acid composition. The process comprises oxidizing at least one oxidizable compound in an oxidizable raw material stream in the presence of an oxidizing gas stream, solvent stream, and at least one catalyst system.

More particularly, the present invention relates to a process to produce a carboxylic acid composition comprising furan-2,5-dicarboxylic acid (FDCA) and compositions thereof. The process comprises oxidizing 5-hydroxylmethyl)furfural in the presence of oxygen, a saturated organic acid solvent having from 2-6 carbon atoms, and a catalyst system at a temperature of about 100° C. to about 220° C. to produce the carboxylic acid composition comprising furan-2,5-dicarboxylic acid.

BACKGROUND OF THE INVENTION

Aromatic dicarboxylic acids, such as terephthalic acid and isophthalic acid, are used to produce a variety of polyester products. Important examples of which are poly (ethylene terephthalate) and its copolymers. These aromatic dicarboxylic acids are synthesized by the catalytic oxidation of the corresponding dialkyl aromatic compounds which are obtained from fossil fuels, which is disclosed in U.S. Patent Application 2006/0205977 A1), which is herein incorporated by reference to the extent it does not contradict the statements herein.

There is a growing interest in the use of renewable resources as feed stocks for the chemical industry mainly due to the progressive reduction of fossil reserves and their related environmental impacts. Furan-2,5-dicarboxylic acid (FDCA) is a versatile intermediate considered as a promising closest biobased alternative to terephthalic acid and isophthalic acid. Like aromatic diacids, FDCA can be condensed with diols such as ethylene glycol to make polyester resins similar to polyethylene terephthalate (PET) (Gandini, A.; Silvestre, A. J; Neto, C. P.; Sousa, A. F.; Gomes, M. *J. Poly. Sci. A* 2009, 47, 295.). Therefore, there is a need in the chemical industry for an efficient process to produce carboxylic acid compositions, especially FDCA. A high yield process (minimum of 90% FDCA yield) to produce a dry, purified FDCA product is provided herein.

DETAILED DESCRIPTION

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

Figure 1:
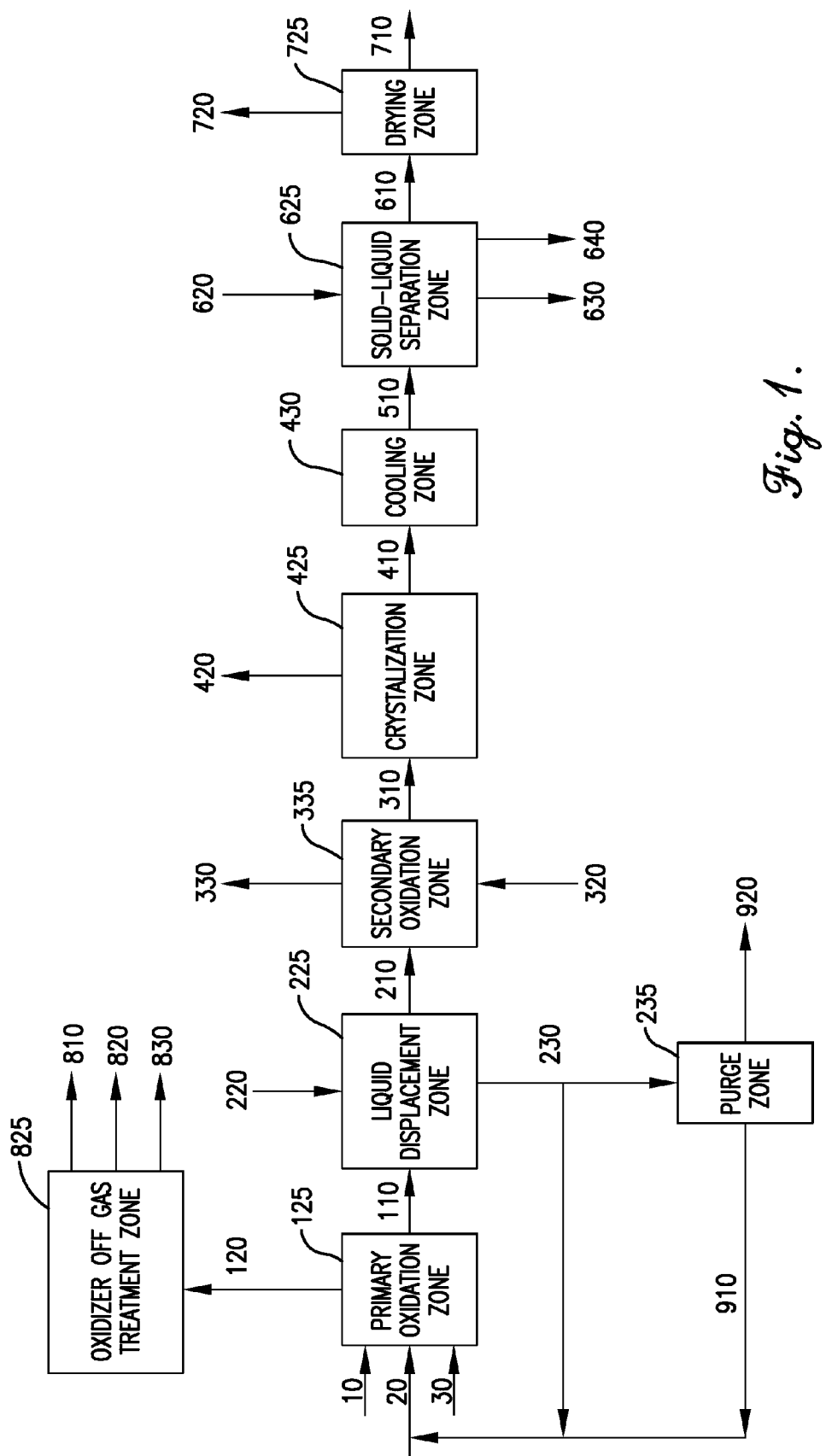
FIG. 1 illustrates different embodiments of the invention wherein a process to produce a dried purified carboxylic acid 710 is provided.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/−19° F.), and a narrow numerical range of 53° F. to 71° F. (62° F.−/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively In one embodiment of the invention, a process is provided to produce carboxylic acid composition and/or dry purified carboxylic acid 710 comprising furan-2,5-dicarboxylic acid (FDCA). Embodiments of the process are represented in FIG. 1. The process comprises oxidizing at least one oxidizable compound in an oxidizable raw material stream 30 in the presence of an oxidizing gas stream 10, solvent stream 20, and at least one catalyst system. The oxidizable raw material stream 30 comprises at least one oxidizable compound suitable to produce a carboxylic acid composition 110 comprising FDCA. The amount of FDCA in the carboxylic acid composition 110 can range from greater than 10 by weight percent in the carboxylic acid composition 110, greater than 20 by weight percent in the carboxylic acid composition 110, greater than 30 by weight percent in the carboxylic acid composition 110. The carboxylic acid composition 110 comprises FDCA and solvent.

In another embodiment of the invention, the process comprises oxidizing at least one oxidizable compound in an oxidizable raw material stream 30 in the presence of an oxidizing gas stream 10, solvent stream 20, and at least one catalyst system. The oxidizable raw material stream 30 comprises at least one oxidizable compound selected from the group consisting of 5-(hydroxymethyl)furfural (5-HMF), 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feedstocks of 5-HMF and 5-HMF esters, mixed feedstocks of 5-HMF and 5-HMF ethers, mixed feedstocks of 5-HMF and 5-alkyl furfurals to generate a carboxylic acid composition comprising FDCA. The process can optionally include removing impurities from the carboxylic acid composition 110 in a liquid displacement zone 225 to form a low impurity slurry stream 210. The low impurity slurry stream 210 can be further treated in a secondary oxidation zone 335 to produce a secondary oxidation slurry stream 310 which can be routed to a crystallization zone 425 to form a crystallized slurry stream 410. The crystallized slurry stream 410 is cooled in a cooling zone 430 and the cooled crystallized slurry stream 510 can be routed to a solid-liquid separation zone 625 to generate a purified wet cake stream 610 comprising FDCA that is dried in a drying zone 725 to generate a dried, purified carboxylic acid 710 comprising purified FDCA.

In one embodiment of the invention, a process is provided to produce a dried, purified carboxylic acid 710 comprising dried, purified furan-2,5-dicarboxylic acid (FDCA) and comprises the following steps:

Step (a) comprises oxidizing at least one oxidizable compound in an oxidizable raw material stream 30 in the presence of an oxidizing gas stream 10, solvent stream 20, and at least one catalyst system in a primary oxidation zone 125 which comprises at least one primary oxidizer reactor to produce a carboxylic acid composition 110 comprising furan-2,5-dicarboxylic(FDCA); wherein the oxidizable raw material stream 30 comprises at least one oxidizable compound selected from the group consisting of 5-(hydroxymethyl)furfural (5-HMF), 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feedstocks of 5-HMF and 5-HMF esters, mixed feedstocks of 5-HMF and 5-HMF ethers, and mixed feedstocks of 5-HMF and 5-alkyl furfurals. Structures for the various oxidizable raw material compounds are outlined below:

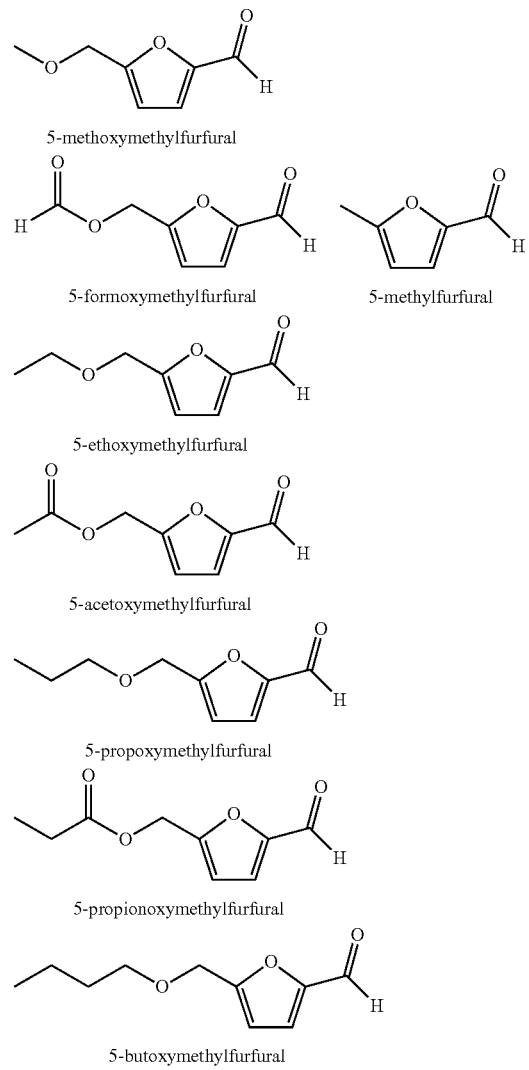

Preferred 5-HMF Derivative Feeds 5-methoxymethylfurfural 5-formoxymethylfurfural 5-methylfurfural 5-ethoxymethylfurfural 5-acetoxymethylfurfural 5-propoxymethylfurfural 5-propionoxymethylfurfural 5-butoxymethylfurfural

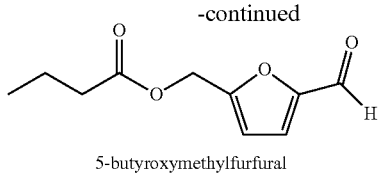

5-butyroxymethylfurfural

The 5-HMF or its derivatives are oxidized with elemental $O_2$ in a multi-step reactions, eqs 1 and 2, to form FDCA with 5-formyl furan-2-carboxylic acid (FFCA) as a key intermediate.

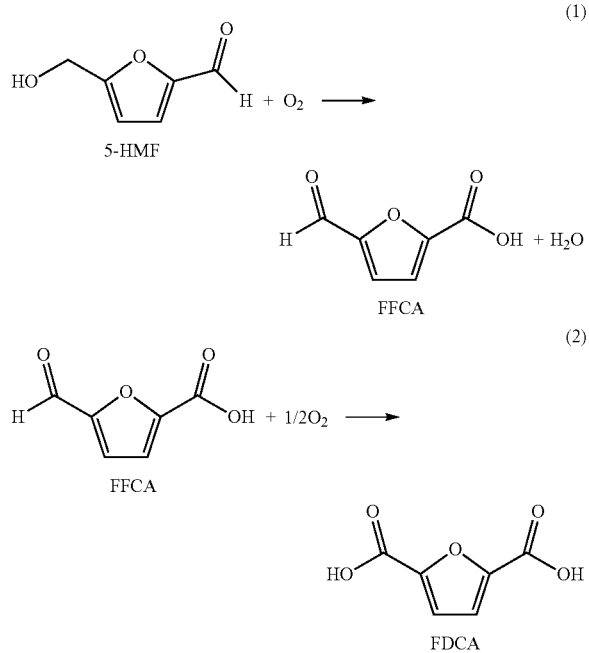

In one embodiment of this invention, streams routed to the primary oxidation zone 125 comprises an oxidizing gas stream 10 comprising oxygen and a solvent stream 20 comprising solvent, an oxidizable raw material stream 30, and a catalyst system. Oxidizable raw material stream 30 comprises a continuous liquid phase. In another embodiment of the invention, the oxidizable raw material stream 30, the oxidizing gas stream 10, the solvent stream 20 and the catalyst system can be fed to the primary oxidization zone 125 as separate and individual streams or combined in any combination prior to entering the primary oxidation zone 125 wherein said feed streams may enter at a single location or in multiple locations in the primary oxidization zone 125.

The carboxylic acid composition 110 comprises FDCA and FFCA. In another embodiment the FFCA in the carboxylic acid composition 110 ranges from about 0.1 wt % (weight percent) to about 4 wt % or 0.1 wt % to about 0.5 wt %, or 0.1wt % to about 1wt %. In another embodiment of the invention the carboxylic acid composition 110 comprises FDCA and FFCA and at least one of 2,5-diformylfuran in an amount ranging from 0 wt % to about 0.2 wt %, levulinic acid in an amount ranging from 0 wt % to 0.5 wt %, succinic acid in an amount ranging from 0 wt % to 0.5 wt % and acetoxy acetic acid in an amount ranging from 0 wt % to 0.5 wt %.

eIn another embodiment of the invention the carboxylic acid composition 110 comprises FDCA, FFCA and EFCA. In other embodiment of the invention the EFCA in the carboxylic acid composition 110 in an range from about 0.05 wt % to 4 wt %, or about 1 wt % to 2 wt %.

The catalyst system comprises at least one catalyst suitable for oxidation. Any catalyst known in the art capable of oxidizing the oxidizable compound can be utilized. Example of suitable catalysts comprise at least one selected from, but are not limited to, cobalt, bromine and manganese compounds, which are soluble in the selected oxidation solvent. In another embodiment of the invention, the catalyst system comprises cobalt, manganese and bromine wherein the weight ratio of cobalt to manganese in the reaction mixture is from about 10 to about 400 and the weight ratio of cobalt to bromine is from about 0.7 to about 3.5.

The oxidizing gas stream comprises oxygen. Examples include, but are not limited to, air and purified oxygen. The amount of oxygen in the primary oxidation zone ranges from about 5 mole % to 45 mole %, 5 mole to 60 mole % 5 mole % to 80 mole %.

Suitable solvents include water and the aliphatic solvents. In an embodiment of the invention, the solvents are aliphatic carboxylic acids which include, but are not limited to, aqueous solutions of $C_2$ to $C_6$ monocarboxylic acids, e.g., acetic acid, propionic acid, n-butyric acid, isobutyric acid, n-valeric acid, trimethylacetic acid, caprioic acid, and mixtures thereof. In another embodiment of the invention, the solvent is volatile under the oxidation reaction conditions to allow it to be taken as an off-gas from the oxidation reactor. In yet another embodiment of the invention the solvent selected is also one in which the catalyst composition is soluble under the reaction conditions.

The most common solvent used for the oxidation is an aqueous acetic acid solution, typically having a concentration of 80 to 99 wt. %. In especially preferred embodiments, the solvent comprises a mixture of water and acetic acid which has a water content of 0% to about 15% by weight. Additionally, a portion of the solvent feed to the primary oxidation reactor may be obtained from a recycle stream obtained by displacing about 80 to 90% of the mother liquor taken from the crude reaction mixture stream discharged from the primary oxidation reactor with fresh, wet acetic acid containing about 0 to 15% water.

Suitable solvents include, but are not limited to, aliphatic mono-carboxylic acids, preferably containing 2 to 6 carbon atoms and mixtures thereof and mixtures of these compounds with water. Examples of aliphatic mono-carboxylic acids, include, but are not limited to acetic acid.

Generally, the oxidation temperature can vary from about 100° C. to about 220° C. and from about 110° C. to about 160° C.

In another embodiment of the invention, a process is provided to produce furan-2,5-dicarboxylic acid (FDCA) in high yields by liquid phase oxidation that minimizes solvent and starting material loss through carbon burn. The process comprises oxidizing at least one oxidizable compound in an oxidizable raw material stream 30 in the presence of an oxidizing gas stream 10, solvent stream 20, and at least one catalyst system in a primary oxidation zone 125; wherein the oxidizable compound is at least one selected from the group consisting of H(C=O)—R—(C=O)H, HOH2C—R—(C=O)H, and 5-(hydroxymethyl)furfural (5-HMF). The oxidizable compound can be oxidized in a solvent comprising acetic acid with or without the presence of water with oxygen in the presence of a catalyst system comprising cobalt, manganese and bromine, wherein the weight ratio of cobalt to manganese in the reaction mixture is from about 10 to about 400 and the weight ratio of cobalt to bromine is from about 0.7 to about 3.5. Such a catalyst system with improved Co:Mn ratio can lead to high yield of FDCA. In this process, the oxidation temperature can vary from about 100° C. to about 220° C., or another range from about 110° C. to about 160° C., which can minimize carbon burn. The cobalt concentration of the catalyst can range from about 1000 ppm to about 6000 ppm, and the amount of manganese from about 2 ppm to about 600 ppm, and the amount of bromine from about 300 ppm to about 4500 ppm with respect to the total weight of the liquid in the reaction medium of the primary oxidation zone 125. As used herein, process temperature is the temperature of the reaction mixture within the primary oxidation zone where liquid is present as the continuous phase. The primary oxidizer reactor will typically be characterized by a lower section where gas bubbles are dispersed in a continuous liquid phase. Solids can also be present in the lower section. In the upper section of the primary oxidizer, gas is in the continuous phase and entrained liquid drops can also be present.

In various embodiments of the invention, the catalyst compositions employed in the processes of the invention comprise cobalt atoms, manganese atoms, and bromine atoms, supplied by any suitable means, as further described below. The catalyst composition is typically soluble in the solvent under reaction conditions, or it is soluble in the reactants fed to the oxidation zone. Preferably, the catalyst composition is soluble in the solvent at 40° C. and 1 atm, and is soluble in the solvent under the reaction conditions.

The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate.

The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrobromic acid, sodium bromide, ammonium bromide, potassium bromide, and tetrabromoethane. Hydrobromic acid, or sodium bromide may be preferred bromine sources.

In another embodiment of the invention, a process is provided for producing furan-2,5-dicarboxylic acid (FDCA) in high yields by liquid phase oxidation that minimizes solvent and starting material loss through carbon burn. The process comprises oxidizing at least one oxidizable compound in an oxidizable raw material stream 30 in the presence of an oxidizing gas stream 10, solvent stream 20, and at least one catalyst system in a primary oxidation zone 125; wherein the oxidizable compound is selected from the group consisting of 5-(acetoxymethyl)furfural (5-AMF), 5-(ethoxymethyl)furfural (5-EMF), 5-methyl furfural (5-MF); wherein the solvent stream 20 comprises acetic acid with or without the presence of water; wherein the catalyst system comprising cobalt, manganese and bromine, wherein the weight ratio of cobalt to manganese in the reaction mixture ranges from about 10 to about 400 and the weight ratio of cobalt to bromine is from about 0.7 to about 3.5. The catalyst system with improved Co:Mn ratio can lead to high yield of FDCA. In this process, the oxidation temperature can vary from about 100° C. to about 220° C., or from about 110° C. to about 160° C. to minimize carbon burn. The cobalt concentration in the catalyst system can range from about 500 ppm to about 6000 ppm, and the amount of manganese from about 2 ppm to about 600 ppm and the amount of bromine from about 300 ppm to about 4500 ppm with respect to the total weight of the liquid in the reaction medium. Mixed feedstocks of 5-AMF and 5-HMF or 5-EMF and 5-HMF or 5-MF and 5-HMF or 5-AMF, 5-EMF and 5-HMF, with varying ratios of the components can be used and similar results can be obtained.

In another embodiment of the invention, a process is provided for producing furan-2,5-dicarboxylic acid (FDCA) in high yields by liquid phase oxidation that minimizes solvent and starting material loss through carbon burn. The process comprises oxidizing at least one oxidizable compound in an oxidizable raw material stream 30 in the presence of an oxidizing gas stream 10, solvent stream 20, and at least one catalyst system in a primary oxidation zone 125; wherein said oxidizable compound is 5-(hydroxymethyl)furfural (5-HMF); wherein said solvent stream comprises acetic acid with or without the presence of water; wherein said catalyst system comprising cobalt, manganese and bromine, wherein the weight ratio of cobalt to manganese in the reaction mixture is from about 10 to about 400. In this process, the temperature can vary from about 100° C. to about 220° C., from about 105° C. to about 180° C., from about 120° C. to about 180° C., from about 120° C. to about 200° C., from about 110° C. to about 180° C., from about 105° C. to about 170° C., from about 110° C. to about 190° C., from about 110° C. to about 190° C., from about 120° C. to about 190° C. and from about 110° C. to about 160° C. The cobalt concentration of the catalyst system can range from about 1000 ppm to about 6000 ppm, and the amount of manganese can range from about 2 ppm to about 600 ppm, and the amount of bromine can range from about 300 ppm to about 4500 ppm with respect to the total weight of the liquid in the reaction medium.

In another embodiment of the invention, the process comprises oxidizing at least one oxidizable compound in an oxidizable raw material stream 30 in the presence of an oxidizing gas stream 10, solvent stream 20, and at least one catalyst system in a primary oxidation zone 125; wherein said oxidizable compound is 5-(hydroxymethyl)furfural (5-HMF); wherein said solvent stream comprises a saturated organic acid having from 2-6 carbon atoms with or without the presence of water at a temperature of 100° C. to 220° C. to produce a dicarboxylic acid composition; wherein the primary oxidation zone 125 comprises at least one primary oxidation reactor and wherein the catalyst system comprises cobalt in a range from about 500 ppm by weight to about 6000 ppm by weight with respect to the weight of the liquid in the reaction medium, manganese in an amount ranging from about 2 ppm by weight to about 600 ppm by weight with respect to the weight of the liquid in the reaction medium and bromine in an amount ranging from about 300 ppm by weight to about 4500 ppm by weight with respect to the weight of the liquid in the reaction medium.

In another embodiment of the invention, when the oxidizable raw material stream 30 comprises 5-HMF, then the cobalt to manganese ratio by weight is at least 10:1, 15:1, 20:1, 25:1, 30:1, 40:1 50:1, 60:1, or 400 to 1.

In another embodiment of the invention, when the oxidizable material stream 30 comprises at least one oxidizable compound selected from the group consisting of 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feedstocks of 5-HMF and 5-HMF esters, mixed feedstocks of 5-HMF and 5-HMF ethers, and mixed feed-stocks of 5-HMF and 5-alkyl furfurals, the cobalt to manganese ratio by weight of the catalyst system is at least 1:1, 10:1, 20:1, 50:1, 100:1, or 400:1.

In another embodiment of this invention, furan-2,5-dicarboxylic acid (FDCA) can be obtained by liquid phase oxidation of 5-(hydroxymethyl)furfural (5-HMF), 5-(acetoxymethyl)furfural (5-AMF) and 5-(ethoxymethyl)furfural (5-EMF) with molecular oxygen using Co/Mn/Br catalyst system in acetic acid solvent. After the oxidation of 5-HMF/5-AMF/5-EMF in presence of acetic acid, the FDCA precipitates out of solution. After filtration, washing with acetic acid and then with water, and drying, solids were obtained with a minimum of 90%, 92%, 94%, 96% FDCA content by weight.

In another embodiment of the invention, FDCA is obtained by liquid phase oxidation of 5-HMF, 5-AMF and 5-EMF with molecular oxygen using Co/Mn/Br catalyst system in acetic acid solvent. After the oxidation of 5-HMF/5-AMF/5-EMF in acetic acid, the FDCA precipitates out of solution. After filtration, washing with acetic acid and then with water, and drying, solids were obtained with a minimum of 96% FDCA content and a maximum b* of 9, or 10, or 11, or 12, or 13, or 14, or 15, or 16, or 17, or 18, or 19, or 20.

The b* is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

In another embodiment of the invention, a process is provided for producing furan-2,5-dicarboxylic acid (FDCA) in minimum yields of 80% or 85% or 90% or greater by liquid phase oxidation that minimizes solvent and starting material loss through carbon burn. As used herein, yield is defined as mass of FDCA obtained divided by the theoretical amount of FDCA that should be produced based on the amount of raw material use. For example, if one mole or 126.11 grams of 5-HMF are oxidized, it would theoretically generate one mole or 156.01 grams of FDCA. If for example, the actual amount of FDCA formed is only 150 grams, the yield for this reaction is calculated to be =(150/156.01) times 100, which equals a yield of 96%. The same calculation applies for oxidation reaction conducted using 5-HMF derivatives or mixed feeds.

In another embodiment of this invention, a process is provided comprising oxidizing at least one oxidizable compound in an oxidizable raw material stream 30 in the presence of an oxidizing gas stream 10, solvent stream 20, and at least one catalyst system in a primary oxidation zone 125; wherein said oxidizable compound is selected from the group consisting of H(C=O)—R—(C=O)H, HOH2C—R—(C=O)H, 5-(hydroxymethyl)furfural (5-HMF); wherein said solvent stream comprises acetic acid with or without the presence of water; wherein said catalyst system comprises cobalt, manganese and bromine, wherein the weight ratio of cobalt to manganese in the reaction mixture is from about 10 to about 400 and the weight ratio of cobalt to bromine is from about 0.7 to about 3.5. Such a catalyst system with improved Co:Mn and Co:Br ratio can lead to high yield of FDCA (minimum of 90%), decrease in the formation of impurities (measured by b*) causing color in the downstream polymerization process while keeping the amount of CO and $CO_2$ in the off-gas at a minimum.

The temperature in the primary oxidation zone can range from about 100° C. to about 220° C., and can range from about 110° C. to about 160° C. or can range from about 105° C. to about 180° C. or about 100° C. to about 200° C., or about 100° C. to about 190° C., or can range from about 105° C. to about 170° C., or can range from about 110° C. to about 180° C., or can range from about 110° C. to about 170° C., or can range from about 110° C. to about 190° C., or can range from about 120° C. to about 180° C., or can range from about 120° C. to about 160° C., or can range from about 120° C. to about 200° C., or can range from about 140° C. to about 180° C., or can range from about 140° C. to about 190° C., or can range from about 140° C. to about 200° C., or can range from about 130° C. to about 180° C., or can range from about 125° C. to about 180° C., or can range from about 130° C. to about 160° C., or can range from about 130° C. to about 170° C. One advantage of the disclosed primary oxidation conditions is low carbon burn as illustrated in Table 1. Oxidizer off gas stream 120 is routed to the oxidizer off gas treatment zone 825 to generate an inert gas stream 810, liquid stream 820 comprising water, and a recovered solvent stream 830 comprising condensed solvent. In one embodiment, at least a portion of recovered solvent stream 830 is routed to wash fed stream 620 and the combined stream is routed to the solid-liquid separation zone 625 for the purpose of washing the solids present in the solid-liquid separation zone 625. In one embodiment, the inert gas stream 810 can be vented to the atmosphere. In another embodiment, at least a portion of the inert gas stream 810 can be used as an inert gas in the process for inerting vessels and or used for conveying gas for solids in the process.

In another embodiment of the invention, the composition of the liquid phase within the primary oxidizer can have a pH from about −4.0 to about 1.0 or the feedstock pH is from about −1.8 to about 1.0, or the feedstock pH is from about −1.5 to about 1.0.

It should be understood that steps (b)-(g) are optional and only one possible embodiment of a process to purified the carboxylic acid composition.

Step (b) comprises routing the crude carboxylic composition 110 and fresh solvent stream 220 to a liquid displacement zone 225 to produce a displaced mother liquor stream 230 and low impurity slurry stream 210 comprising FDCA. The displaced mother liquor stream 230 comprises solvent and soluble matter dissolved in the solvent comprising dissolved impurities and dissolved catalyst. In various embodiments of the invention, from about 5% to about 99%, from about 30% to about 90%, and most preferably from about 50 to about 85% of mother liquor present in the carboxylic acid composition 110 is displaced in the liquid displacement zone 225 resulting in dissolved matter comprising impurities present in the displaced mother liquor not going forward in the process. Sufficient fresh solvent is fed to the liquid displacement zone 225 that becomes mixed with solids present resulting in a low impurity slurry stream 210 being pumpable with weight % solids ranging from 1% to 50%, 10% to 40%, and preferably the weight % solids in stream 210 will range from 25% to 38%.

The liquid displacement zone may be a single unit operation or multiple unit operations. In one embodiment of the invention, the liquid displacement zone 225 may be any solid-liquid separation device capable of generating an isolated wet cake from a feed slurry and then mixing the isolated wet cake with fresh solvent in a separate mixing device to generate the low impurity slurry stream 210. Examples of suitable solid-liquid separation devices include, but are not limited to, a continuous pressure drum filter, solid bowl centrifuges including, but not limited to, decanter and disc stack centrifuges, and batch pressure filters including, but not limited to, candle and leaf filters. The preferred solid-liquid separation device for this application is a continuous pressure drum filter. The solid-liquid separator is operated at temperatures between about 30 degrees C. to about 200 degrees C., preferably 80 degrees C. to about 170.degree. C. The solid-liquid separator in the liquid displacement zone 225 may be operated in continuous or batch mode, although it will be appreciated that for commercial processes, the continuous mode is preferred. Alternatively, a portion of the mother liquor in stream 110 is displaced with fresh liquor stream 220 in a single device to form the low impurity slurry stream 210 without forming an isolated wet cake.

In one embodiment, from 5% to 100% by weight of the displaced mother liquor stream 230 is routed to a purge zone 235 wherein a portion of the impurities present in stream 230 are isolated and exit the process as purge stream 920, wherein a portion is 5% by weight or greater. Recovered solvent stream 910 comprises solvent and catalyst isolated from stream 230 and is recycled to the process. In one embodiment, recovered solvent stream 910 is recycled to the primary oxidation zone 125 and contains greater than 30% of the catalyst that entered the purge zone 235 in stream 230. In another embodiment, stream 910 is recycled to the primary oxidation zone 125 and contains greater than 50 weight %, contains greater than 70 weight %, and preferably greater than 90 weight % of the catalyst that enters the purge zone 235 in stream 230 on a continuous or batch basis.

In another embodiment of this invention, a portion up to 100% of the carboxylic acid composition 110 may be routed directly to a secondary oxidation zone 335 without being subjected to the liquid displacement zone 225. In another embodiment of the invention, up to 100% of the feed to the purge zone 235 may be a mother liquor stream 630 generated in a solid-liquid separation zone 625 which also produces the purified wet cake stream 610.

In yet another embodiment, up to 100% of the feed to the purge zone 235 may be mother liquor generated in a secondary liquid displacement zone located at some location downstream of the secondary oxidation zone 325. A secondary liquid displacement zone is not show in FIG. 1, and it comprises equipment like that described for the liquid displacement zone 225 located after the primary oxidation zone 125, and must be located after the secondary oxidation zone 335.

Step (c) comprises oxidizing the low impurity slurry stream 210 in a secondary oxidation zone 335 to form a purified slurry stream 310. In one embodiment of the invention, the low impurity slurry stream 210 is routed to a secondary oxidation zone 335 where it is heated to between about 115 degrees C. and about 220 degrees C., and preferably between about 120 degrees C. to about 200 degrees C. and further oxidized with an oxidizing gas, such as air, fed by line 320 to produce a purified slurry stream 310. The secondary oxidation zone comprises at least one oxidation reactor vessel. In one embodiment, the secondary oxidation zone can be one or more oxidation vessels. When the carboxylic acid in low impurity slurry stream 210 is FDCA, the secondary oxidation zone is operated at a temperature ranging from about 115 degrees C. to about 220 degrees C., preferably between about 120 degrees C. to about 200 degrees C., and stream 210 is further oxidized with an oxidizing gas stream fed by line 320 to produce a purified slurry stream 310.

Generally, oxidation in the secondary oxidation zone 335 is at a higher temperature than the oxidation in the primary oxidation zone 125 to enhance the impurity removal. In one embodiment, the secondary oxidation zone 335 is operated at about 30° C., 20° C., and preferably 10° C. higher temperature than the oxidation temperature in the primary oxidation zone 125 to enhance the impurity removal. The secondary oxidation zone 335 can be heated directly with solvent vapor, or steam via stream 320 or indirectly by any means known in the art.

Additional purification of the low impurity slurry stream 210 is accomplished in the secondary oxidation zone by a mechanism involving recrystallization or crystal growth and oxidation of impurities and intermediates including FFCA. One of the functions of the secondary oxidation zone is to convert FFCA to FDCA. FFCA is considered monofunctional relative to a polyester condensation reaction because it contains only one carboxylic acid. FFCA is present in the carboxylic acid composition stream 110 and the low impurity slurry stream 210. FFCA is generated in the primary oxidation zone 125 because the reaction of 5-HMF to FFCA can be about eight times faster than the reaction of FFCA to the desired di-functional product FDCA. Additional air or molecular oxygen may be fed in stream 320 to the secondary oxidation zone 335 in an amount necessary to oxidize a substantial portion of the partially oxidized products such as FFCA in the stream 210 to the corresponding carboxylic acid FDCA. Generally, at least 70% by weight of the FFCA present in the low impurity slurry stream 210 is converted to FDCA in the secondary oxidation zone 335. Preferably, at least 80% by weight of the FFCA present in the low impurity slurry stream 210 is converted to FDCA in the secondary oxidation zone 335, and most preferably, at least 90% by weight of the FFCA present in the low impurity slurry stream 210 is converted to FDCA in the secondary oxidation zone 335. Significant concentrations of monofunctional molecules like FFCA in the dried, purified FDCA product are particularly detrimental to polymerization processes as they may act as chain terminators during the polyester condensation reaction.

The amount of oxygen fed in the secondary oxidation zone 335 in controlled to limit the burning of organic molecules to $CO_2$. The amount of oxygen in stream 330 is monitored and used to control the amount of oxygen fed in stream 320. Another function of the secondary oxidation zone 335 is to dissolve and recrystallize solids present in the low impurity slurry stream 210 fed to the secondary oxidation zone. At least 10% by weight, 25% by weight, 50% by weight, and preferably at least 85% by weight of solid impurities and oxidation by-products in stream 210 feed to the secondary oxidation zone 335 go into solution as the FDCA particles are dissolved and re-crystallized in the secondary oxidation zone 335. Off gas from the secondary oxidation zone is withdrawn via line 330 and fed to a recovery system where the solvent is removed from the off gas comprising volatile organic compounds (VOCs). VOCs including methyl bromide may be treated, for example by incineration in a catalytic oxidation unit. The purified slurry stream 310 generated in the secondary oxidation zone is routed to the crystallization zone 425.

Step (d) comprises crystallizing the secondary oxidation slurry 310 in a crystallization zone 425 to form a crystallized slurry stream 410. Generally, the crystallization zone 425 comprises at least one crystallizer. Vapor from the crystallization zone can be condensed in at least one condenser and returned to the crystallization zone 425 or routed away from crystallization zone 425. Optionally, the liquid from the condenser or vapor product from the crystallization zone can be recycled, or it can be withdrawn or sent to an energy recovery device. In addition, the crystallizer off gas is removed via line 420 and can be routed to a recovery system where the solvent is removed, and crystallizer off gas comprising VOCs may be treated, for example, by incineration in a catalytic oxidation unit. When the carboxylic acid is FDCA, the purified slurry stream 310 from the secondary oxidation zone 335 is fed to a crystallization zone 425 comprising at least one crystallizer where it is cooled to a temperature between about 40.degrees C. to about 175 degrees C. to form a crystallized slurry stream 410, preferably to a temperature between about 50 degrees C. to about 170 degrees C., and most preferably from about 60 degrees C. to about 165 degrees C.

The crystallized slurry stream 410 is then routed to a cooling zone 430 to generate a cooled crystallized slurry stream 510. The cooling of the crystallized slurry stream 410 can be accomplished by any means known in the art. Typically, the cooling zone 430 comprises a flash tank. The temperature of stream 510 can range from 35° C. to 160° C., 45° C. to 120° C., and preferably from 55° C. to 95° C.

In another embodiment, a portion of up to 100% of the secondary oxidation slurry stream 310 is routed directly to the cooling zone 425, thus the portion is not subjected to a crystallization zone 430. In yet another embodiment, a portion of up to 100% of the crystallized slurry stream 410 is routed directly to a secondary liquid displacement zone which is not illustrated in FIG. 1. Up to 100% of the slurry effluent comprising FDCA from a secondary liquid displacement zone can be routed to the solid-liquid separation zone 625 and or routed directly to the cooling zone 430. The function of the secondary liquid displacement zone is to displace a portion of solvent in the crystallized slurry stream 410 with fresh solvent and or water wherein a portion must be greater than 5 weight percent. The secondary liquid displacement zone is separate and distinct from the liquid displacement zone 225 located after the primary oxidation zone 125. The same type of equipment may be used for both the primary and secondary liquid displacement zones. In yet another embodiment, crystallized slurry stream 410 can be routed directly to the solid-liquid separation zone 625 without being first processed in the cooling zone 430.

Step (e) comprises isolating, washing, and dewatering solids present in the cooled, crystallized slurry stream 510 in the solid-liquid separation zone 625. These functions may be accomplished in a single solid-liquid separation device or multiple solid-liquid separation devices. The solid-liquid separation zone 625 comprises at least one solid-liquid separation device capable of separating solids and liquids, washing solids with a wash solvent stream 620, and reducing the % moisture in the washed solids to less than 30 weight %, less than 25 weight %, less than 20 weight %, less than 15 weight %, and preferably less than 10 weight %.

Equipment suitable for the solid liquid separation zone 625 can typically be comprised of, but not limited to, the following types of devices: centrifuges, cyclones, rotary drum filter, belt filters, pressure leaf filters, candle filters, etc. The preferred solid liquid separation device for the solid liquid separation zone 625 is a rotary pressure drum filter. The temperature of the cooled, crystallized slurry stream 510 which is routed to the solid-liquid separation zone 625 can range from 50° C. to 140° C., 70° C. to 120° C., and is preferably from 75° C. to 95° C. The wash solvent stream 620 comprises a liquid suitable for displacing and washing mother liquor from the solids.

In one embodiment of the invention, a suitable wash solvent comprises acetic acid and water. In another embodiment, a suitable solvent comprises water up to 100% water. The temperature of the wash solvent can range from 20° C. to 135° C., 40° C. and 110° C., and preferably from 50° C. to 90° C.

The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3.

After solids are washed in the solid liquid separation zone, they are dewatered. Dewatering involves reducing the mass of moisture present with the solids to less than 30% by weight, less than 25% by weight, less than 20% by weight, less than 15% by weight, and most preferably less than 10% by weight resulting in the generation of a purified wet cake stream 610. In one embodiment, dewatering is accomplished in a filter by passing a gas stream through the solids to displace free liquid after the solids have been washed with a wash solvent. In another embodiment, dewatering is achieved by centrifugal forces in a perforated bowl or solid bowl centrifuge. Stream 630 generated in the solid-liquid separation zone 625 is a mother liquor stream comprising oxidation solvent, catalyst, and some impurities and oxidation byproducts. In one embodiment, a portion of stream 630 is routed to a purge zone 235 and a portion is routed back to the primary oxidation zone 125 wherein a portion is at least 5 weight %. Wash liquor stream 640 is also generated in the solid-liquid separation zone 625 and comprises a portion of the mother liquor present in stream 510 and wash solvent wherein the ratio of mother liquor mass to wash solvent mass is less than 3 and preferably less than 2.

Step (f) comprises drying the purified wet cake stream 610 in a drying zone 725 to generate a dry purified carboxylic acid 710 and a vapor stream 720. In one embodiment, vapor stream 720 comprises wash solvent vapor. In another embodiment, vapor stream 720 comprises oxidation solvent and wash solvent. The drying zone 725 comprises at least one dryer and can be accomplished by any means known in the art that is capable of evaporating at least 10% of the volatiles remaining in the purified wet cake stream 610 to produce the dried, purified carboxylic acid 710 comprising purified FDCA and a vapor stream 720. For example, indirect contact dryers include, but are not limited to, a rotary steam tube dryer, a Single Shaft Porcupine® dryer, and a Bepex Solidaire® dryer. Direct contact dryers include, but are not limited to, a fluid bed dryer and drying in a convey line can be used for drying to produce stream 710. The dried, purified carboxylic acid 710 comprising purified FDCA can be a carboxylic acid composition with less than 8% moisture, preferably less than 5% moisture, and more preferably less than 1% moisture, and even more preferably less than 0.5%, and yet more preferably less than 0.1%. In another embodiment of this invention, if the liquid portion of the purified wet cake stream 610 comprises water and contains less than 0.1 weight % acetic acid, less than 500 ppm wt acetic acid, and preferably less than 200 ppm wt, the stream 610 can be fed directly to a polymerization zone without first being dried.

In one embodiment of the invention, a vacuum system can be utilized to draw vapor stream 720 from the drying zone 725. If a vacuum system is used in this fashion, the pressure of stream 720 at the dryer outlet can range from about 760 mmHg to about 400 mmHg, from about 760 mmHg to about 600 mmHg, from about 760 mmHg to about 700 mmHg, from about 760 mmHg to about 720 mmHg, and from about 760 mmHg to about 740 mmHg wherein pressure is measured in mmHg above absolute vacuum. The contents of the conduit between solid-liquid separation zone 625 and drying zone 725 utilized to transfer the purified wet cake stream 610 comprises wet cake stream and gas wherein gas is the continuous phase. The pressure at the exit of the solid liquid separation zone 625 can be close to that of the pressure where vapor stream 720 exits the drying zone 725, wherein close is defined as within 2 psig, within 0.8 psig, and preferably within 0.4 psig.

In an embodiment of the invention, the dried, purified carboxylic acid 710 has a b* less than about 9.0. In another embodiment of the invention, the b* color of the dried, purified carboxylic acid 710 is less than about 6.0. In another embodiment of the invention, the b* color of the dried, purified carboxylic acid 710 is less than about 5.0. In another embodiment of the invention, the b* color of the dried, purified carboxylic acid 710 is less than about 4.0. In another embodiment of the invention, the b* color of the dried, purified carboxylic acid 710 is less than about 3. The b* color is one of the three-color attributes measured on a spectroscopic reflectance-based instrument. A Hunter Ultrascan XE instrument in reflectance mode is typically the measuring device. Positive readings signify the degree of yellow (or absorbance of blue), while negative readings signify the degree of blue (or absorbance of yellow).

It should be appreciated that the process zones previously described can be utilized in any other logical order to produce the dried, purified carboxylic acid 710. It should also be appreciated that when the process zones are reordered that the process conditions may change. It is also understood that all percent values are weight percents.

Step (g) is an optionally step comprising decolorizing the FDCA in this process or an esterified FDCA with a diol stream via hydrogenation. In one embodiment, the diol stream comprises ethylene glycol. In another embodiment, the diol stream comprises isomers of cyclohexane diol, preferably the 1-4 cyclohexane diol isomer. The decolorizing of the FDCA in this process or an esterified FDCA can be accomplished by any means known in the art and is not limited to hydrogenation. However, for example, in one embodiment of the invention, the decolorizing can be accomplished by reacting a carboxylic acid that has undergone esterification treatment, for example with ethylene glycol, with molecular hydrogen in the presence of a hydrogenation catalyst in a reactor zone to produce a decolorized carboxylic acid solution or a decolorized ester product.

For the reactor zone, there are no special limitations in the form or construction thereof, subject to an arrangement that allows supply of hydrogen to effect intimate contact of the carboxylic acid or ester product with the catalyst in the reactor zone. Typically, the hydrogenation catalyst is usually a single Group VIII metal or combination of Group VIII metals. Preferably, the catalyst is selected from a group consisting of palladium, ruthenium, rhodium and combination thereof. The reactor zone comprises a hydrogenation reactor that operates at a temperature and pressure sufficient to hydrogenate a portion of the characteristically yellow compounds to colorless derivatives.

Since numerous modifications and changes will readily occur to those skilled in the art, it is not desired to limit this invention to the exact process and operations illustrated and described above, and accordingly all suitable modifications and equivalents may be resorted to, falling within the scope of the invention.

EXAMPLES

This invention can be further illustrated by the following examples of embodiments thereof, although it will be understood that these examples are included merely for the purposes of illustration and are not intended to limit the scope of the invention unless otherwise specifically indicated.

Examples Set 1

In Examples 1a-3d, glacial acetic acid and the catalyst components in concentrations described in Tables 1, 2 and 3 were transferred to a 300 mL titanium autoclave equipped with a high pressure condenser, a baffle and an Isco pump. Cobalt, manganese and ionic bromine were provided as cobalt (II) acetate tetrahydrate, manganese (II) acetate and sodium bromide and/or aqueous hydrobromic acid respectively. The autoclave was pressurized with approximately 50 psig of nitrogen and the homogeneous mixture was heated to the desired temperature in a closed system (i.e., with no gas flow) with stirring. At reaction temperature, an air flow of 1500 sccm was introduced at the bottom of the solution and the reaction pressure was adjusted to the desired pressure. A solution of 5-HMF/5-AMF/5-EMF in acetic acid was fed to the mixture at a rate of 0.833 mL/min via a high pressure Isco pump (this is t=0 for the reaction time). After 30 seconds from the start of substrate feeding, 1.0 g of peracetic acid in 5.0 mL of acetic acid was introduced using a blow-case to start the reaction. The feed was stopped after 1 h and the reaction continued for an additional hour at the same conditions of air flow, temperature and pressure. After the reaction time was completed, the air flow was stopped and the autoclave was cooled to room temperature and depressurized. The heterogeneous mixture was filtered to isolate the crude FDCA. The mass of the filtrate was recorded. The crude FDCA was washed with 60 mL of acetic acid two times and then twice with 100 mL of DI water. The washed crude FDCA was oven dried at 110° C. under vacuum overnight and then weighed. The solid and the filtrate were analyzed by Gas Chromatography using BSTFA derivatization method.

The Off-gas was analyzed for CO and $CO_2$ by ND-1R (ABB, Advanced Optima) and $O_2$ by a paramagnetism detection system (Servomex, 1440 Model).

Analytical

Gas Chromatographic Method Process samples were analyzed using a Shimadzu gas chromatograph Model 2010 (or equivalent) equipped with a split/heated injector (300° C.) and a flame ionization detector (300° C.). A capillary column (60 meter×0.32 mm ID) coated with (6% cyanopropylphenyl)-methylpolysiloxane at 1.0 µm film thickness (such as DB-1301 or equivalent) was employed. Helium was used as the carrier gas with an initial column head pressure of 29.5 psi and an initial column flow of 3.93 mL/minute while the carrier gas linear velocity of 45 cm/second was maintained constant throughout the entire oven temperature program. The column temperature was programmed as follows: The initial oven temperature was set at 80° C. and was held for 6 minutes, the oven was ramped up to 150° C. at 4° C./minute and was held at 150° C. for 0 minute, the oven was ramped up to 240° C. at 10° C./minute and was held at 240° C. for 5 minutes, then the oven was ramped up to 290° C. at 10° C./minute and was held at 290° C. for 17.5 minutes (the total run time was 60 mins). 1.0-µl of the prepared sample solution was injected with a split ratio of 40:1. EZ-Chrom Elite chromatography data system software was used for data acquisition and data processing. The sample preparation was done by weighing 0.1 g (accurate to 0.1 mg) of sample in a GC vial and adding 200.0 µl ISTD solution (1% by volume of decane in pyridine) and 1000 µl of BSTFA (N,O-bis(trimethylsilyl)trifluoroacetamide) with 1% TMSCl (trimethylchlorosilane) to the GC vial. The content was heated at 80° C. for 30 minutes to ensure complete derivatization. 1.0-μl of this prepared sample solution was injected for GC analysis.

Color Measurement.
1) Assemble the Carver Press die as instructed in the directions—place the die on the base and place the bottom 40 mm cylinder polished side face-up.
2) Place a 40 mm plastic cup (Chemplex Plasticup, 39.7×6.4 mm) into the die.
3) Fill the cup with the sample to be analyzed. The exact amount of sample added is not important.
4) Place the top 40 mm cylinder polished side face-down on the sample.
5) Insert the plunger into the die. No "tilt" should be exhibited in the assembled die.
6) Place the die into the Carver Press, making sure that it is near the center of the lower platen. Close the safety door.
7) Raise the die until the upper platen makes contact with the plunger. Apply >20,000 lbs pressure. Then allow the die to remain under pressure for approximately 3 minutes (exact time not critical).
8) Release the pressure and lower the lower platen holding the die.
9) Disassemble the die and remove the cup. Place the cup into a labeled plastic bag (Nasco Whirl-Pak 4 oz).
10) Using a HunterLab Colorquest XE colorimeter, create the following method (Hunterlab EasyQuest QC software, version 3.6.2 or later)
Mode: RSIN-LAV (Reflectance Specular Included-Large Area View)
Measurements:
CIE L* a* b*
CIE X Y Z
11) Standardize the instrument as prompted by the software using the light trap accessory and the certified white tile accessory pressed against the reflectance port.
12) Run a green tile standard using the certified white tile and compare the CIE X, Y, and Z values obtained against the certified values of the tile. The values obtained should be ±0.15 units on each scale of the stated values.
13) Analyze the sample in the bag by pressing it against the reflectance port and obtaining the spectrum and L*, a*, b* values. Obtain duplicate readings and average the values for the report.

Interpretation of Results:
During the oxidation of 5-HMF to FDCA the alcohol site (ArCH$_2$OH) was converted into carboxylic acid (ArCOOH) mainly via aldehyde (ArCHO), eq 3. Examples 1a, and 1b (Table-1) which use catalyst systems consisting of cobalt, manganese and aqueous hydrobromic acid source produced about 90% yield of FDCA with >98% purity of crude FDCA solid and with a b* of about 6. The crude FDCA solid also contains 5-Formylfuran-2-carboxylic acid (FFCA), only the hydroxylmethyl groups are oxidized to carboxylic acid groups, due to incomplete oxidation.

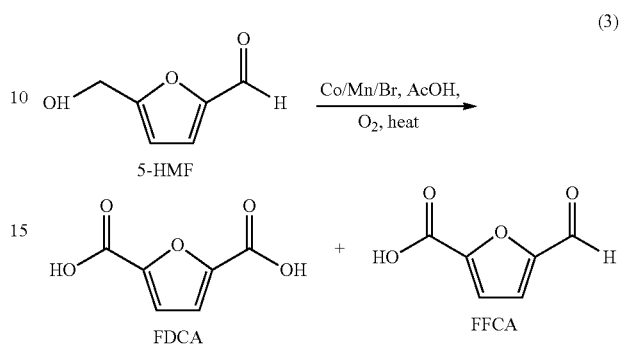

(3)

Oxidation of 5-AMF, which contains an oxidizable ester and aldehydes moieties, produced FDCA, FFCA, and acetic acid, eq 4. Examples 2a to 2b (Table-2) demonstrate that a minimum of 99% purity FDCA solid with a b* of about 7 or less can be achieved using cobalt, manganese and aqueous hydrobromic acid catalyst system.

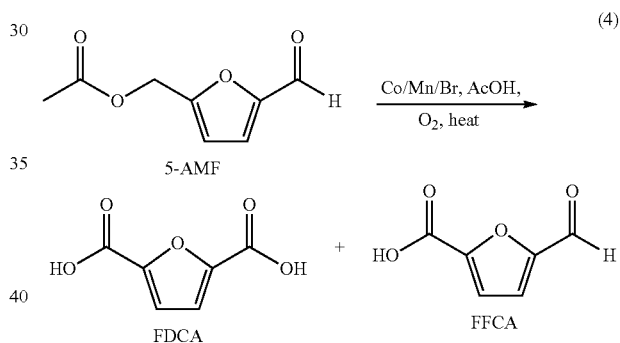

(4)

Oxidation of 5-EMF, which contains an oxidizable ether and aldehyde moieties, produced FDCA, FFCA, 5-(ethoxycarbonyl)furan-2-carboxylic acid (EFCA) and acetic acid, eq 5. Examples 3a to 3d (Table-3) show that a minimum of 96% purity FDCA solid with a b* of about 6 or less can be achieved using cobalt, manganese and aqueous hydrobromic acid catalyst system.

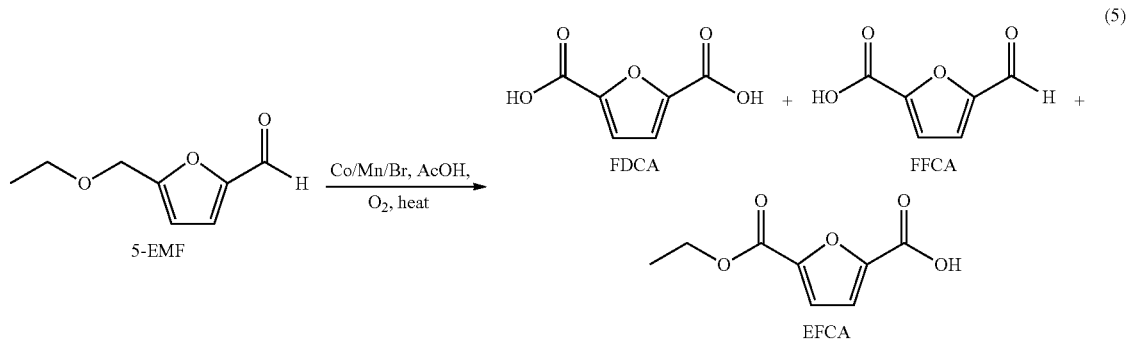

(5)

It is very important to note that in a continuous process under the same conditions as described in this invention report (which was conducted as a batch process) even higher purity of crude FDCA is expected due to efficient mixing, relatively low concentrations of reactive intermediates, and other reasons familiar to those skilled in the art.

TABLE 1

Results from semi-batch reactions performed as described above using 5-HMF feed.*

| Example | Co conc (ppm) | Mn conc (ppm) | Br conc (ppm) | Temp (° C.) | yield of FDCA (%) | yield of FFCA (%) | Solid Composition FDCA | FFCA | b* |
|---|---|---|---|---|---|---|---|---|---|
| 1a | 2000 | 93.3 | 3000 | 132 | 89.4 | 0.58 | 99.20 | 0.81 | 5.845 |
| 1b | 2000 | 93.3 | 3000 | 132 | 88.6 | 0.8 | 98.67 | 0.77 | 6.175 |

*P = 130 psig.

TABLE 2

Results from semi-batch reactions performed as described above using 5-AMF feed.*

| Example | Co conc (ppm) | Mn conc (ppm) | Br conc (ppm) | Temp (° C.) | yield of FDCA (%) | yield of FFCA (%) | Solid Composition FDCA | FFCA | b* |
|---|---|---|---|---|---|---|---|---|---|
| 2a | 2500 | 116.8 | 2500 | 130 | 88.2 | 0.25 | 99.71 | 0.25 | 4.4 |
| 2b | 2000 | 93.5 | 3000 | 130 | 90.2 | 0.16 | 99.44 | 0.16 | 6.8 |

*P = 130 psig.

TABLE 3

Results from semi-batch reactions performed as described above using EMF feed.*

| Example | Co conc (ppm) | Mn conc (ppm) | Br conc (ppm) | Temp (° C.) | yield of FDCA (%) | yield of FFCA (%) | yield of EFCA (%) | Solid Composition FDCA | FFCA | EFCA | b* |
|---|---|---|---|---|---|---|---|---|---|---|---|
| 3a | 2500 | 116.8 | 2500 | 130 | 89.0 | 0.02 | 0.23 | 99.04 | 0.02 | 0.02 | 3.97 |
| 3b | 2500 | 116.8 | 2500 | 130 | 87.4 | 0.42 | 1.31 | 98.08 | 0.42 | 0.04 | 2.74 |
| 3c | 2000 | 93.5 | 3000 | 130 | 88.0 | 0.09 | 0.43 | 99.20 | 0.09 | 0.05 | 5.845 |
| 3d | 2000 | 93.5 | 3000 | 105 | 86.0 | 2.92 | 1.40 | 96.22 | 2.90 | 0.15 | 0.98 |

*P = 130 psig.

Examples Set 2

Air oxidation of 5-HMF using cobalt, manganese and ionic bromine catalysts system in acetic acid solvent were conducted. After reaction the heterogeneous mixture was filtered to isolate the crude FDCA. The crude FDCA was washed with acetic acid two times and then twice with DI water. The washed crude FDCA was oven dried at 110° C. under vacuum overnight. The solid and the filtrate were analyzed by Gas Chromatography using BSTFA derivatization method. b* of the solid was measured using a Hunter Ultrascan XE instrument. As shown in Table 4 we have discovered conditions that to generate yields of FDCA up to 89.4%, b*<6, and low carbon burn (<0.0006 mol/min CO+$CO_2$).

TABLE 4

Results from semi-batch reactions.*

| Example | Bromide source | Co conc (ppm) | Mn conc (ppm) | Br conc (ppm) | yield of FDCA (%) | yield of FFCA (%) | CO (total mol) | $CO_2$ (total mol) | $CO_x$ (mol/min) | pH, before reaction | Color (b*) |
|---|---|---|---|---|---|---|---|---|---|---|---|
| 4a | solid NaBr | 2000 | 93.3 | 3000 | 81.6 | 0.81 | 0.013 | 0.078 | 0.000758 | −0.12 | 13.91 |
| 4b | solid NaBr | 2000 | 93.3 | 3000 | 82.6 | 0.87 | 0.013 | 0.092 | 0.000875 | −0.12 | 14.14 |
| 4c | aqueous HBr | 2000 | 93.3 | 3000 | 89.4 | 8.58 | 0.003 | 0.061 | 0.000533 | −1.03 | 5.845 |
| 4d | aqueous HBr | 2000 | 93.3 | 3000 | 88.6 | 0.8 | 0.0037 | 0.061 | 0.000539 | −1.03 | 6.175 |

*P = 130 psig, $CO_x$ (mol/min) = CO (mol/min) + CO2 (mol/min).

Examples Set 3

In Examples 5a-5h, glacial acetic acid and the catalyst components in concentrations described in Table-5 were transferred to a 300 mL titanium autoclave equipped with a high pressure condenser, a baffle and an Isco pump. Cobalt, manganese and ionic bromine were provided as cobalt (II) acetate tetrahydrate, manganese (II) acetate and sodium bromide and/or aqueous hydrobromic acid respectively. The autoclave was pressurized with approximately 50 psig of nitrogen and then the homogeneous mixture was heated to the desired temperature in a closed system (i.e., with no gas flow) with stirring. At reaction temperature, an air flow of 1500 sccm was introduced at the bottom of the solution and the reaction pressure was adjusted to the desired pressure. A solution of 5-HMF in acetic acid was fed to the mixture at a rate of 0.833 mL/min via a high pressure Isco pump (this is t=0 for the reaction time). After 30 seconds from the start of 5-HMF feeding, 1.0 g of peracetic acid in 5.0 mL of acetic acid was introduced using a blow-case to start the reaction. The feed was stopped after 1 h and the reaction continued for 1 more hour at the same conditions of air flow, temperature and pressure. After the reaction time was completed the air flow was stopped and the autoclave was cooled to room temperature and depressurized. The heterogeneous mixture was filtered to isolate the crude FDCA. The mass of the filtrate was recorded. The crude FDCA was washed with 60 mL of acetic acid two times and then twice with 100 mL of DI water. The washed crude FDCA was oven dried at 110° C. under vacuum overnight and then weighed. The solid and the filtrate were analyzed by Gas Chromatography using BSTFA derivatization method.

The Off-gas was analyzed for CO and $CO_2$ by ND-1R (ABB, Advanced Optima) and $O_2$ by a paramagnetism detection system (Servomex, 1440 Model).

Analytical

Gas Chromatographic Method Process samples were analyzed using a Shimadzu gas chromatograph Model 2010 (or equivalent) equipped with a split/heated injector (300° C.) and a flame ionization detector (300° C.). A capillary column (60 meter×0.32 mm ID) coated with (6% cyanopropylphenyl)-methylpolysiloxane at 1.0 μm film thickness (such as DB-1301 or equivalent) was employed. Helium was used as the carrier gas with an initial column head pressure of 29.5 psi and an initial column flow of 3.93 mL/minute while the carrier gas linear velocity of 45 cm/second was maintained constant throughout the entire oven temperature program. The column temperature was programmed as follows: The initial oven temperature was set at 80° C. and was held for 6 minutes, the oven was ramped up to 150° C. at 4° C./minute and was held at 150 for 0 minute, the oven was ramped up to 240° C. at 10° C./minute and was held at 240 for 5 minutes, then the oven was ramped up to 290° C. at 10° C./minute and was held at 290 for 17.5 minutes (the total run time was 60 mins). 1.0-μl of the prepared sample solution was injected with a split ratio of 40:1. EZ-Chrom Elite chromatography data system software was used for data acquisition and data processing. The sample preparation was done by weighing 0.1 g (accurate to 0.1 mg) of sample in a GC vial and adding 200.0 μl ISTD solution (1% by volume of decane in pyridine) and 1000 μl of BSTFA (N,O-bis(trimethylsilyl)trifluoroacetamide) with 1% TMSCl (trimethylchlorosilane) to the GC vial. The content was heated at 80° C. for 30 minutes to ensure complete derivatization. 1.0-μl of this prepared sample solution was injected for GC analysis.

pH measurement. The electrode for determining non-aqueous pH and millivolts was a Schott N6480-eth series electrode. The LiCl/EtOH filling solution was replaced with $(Et)_4N^+Br^-$/ethylene glycol. The electrode response was monitored by Multi-T 2.2 software through a Jensen Systems cdv-70 series Sensolab interface box. The buffers (pH 4 and 7) were purchased from VWR, and the $(Et)_4N^+Br^-$/ethylene glycol filling solution was from Metrohm.

To perform the pH measurements, a non-aqueous electrode was initially calibrated using aqueous buffers of 4 and 7 allowing the electrode to equilibrate with each for two to three minutes before calibrating at the respective level. Once the electrode was calibrated within 97.5% of 59.2 millivolts slope, the samples were portioned (~15 mL) into smaller vials with mini-Teflon stir bars. The samples were then placed on a stir plate, and the electrode was lowered into the sample. The depth of the electrode was set to where the sample covered about half of the junction slide. Once the sample and electrode was ready, the sample was measured for non-aqueous pH over a period of three minutes. The time was sufficient for equilibration between the electrode and the sample. Between each sample measurement, the electrode was rinsed with Millipore-grade water and wiped with a Kimwipe. The results were recorded in non-aqueous pH units. The millivolts results were also recorded.

Color measurement. 1) Assemble the Carver Press die as instructed in the directions—place the die on the base and place the bottom 40 mm cylinder polished side face-up.

2) Place a 40 mm plastic cup (Chemplex Plasticup, 39.7×6.4 mm) into the die.
3) Fill the cup with the sample to be analyzed. The exact amount of sample added is not important.
4) Place the top 40 mm cylinder polished side face-down on the sample.
5) Insert the plunger into the die. No "tilt" should be exhibited in the assembled die.
6) Place the die into the Carver Press, making sure that it is near the center of the lower platen. Close the safety door.
7) Raise the die until the upper platen makes contact with the plunger. Apply >20,000 lbs pressure. Then allow the die to remain under pressure for approximately 3 minutes (exact time not critical).
8) Release the pressure and lower the lower platen holding the die.

nson, J. H. *Inorg. Chem.* 2000, 39, 1549). The activity of hydrobromic acid or sodium bromide reaction mediums can be increased by addition of a strong Brønsted acid (such as triflic acid, HCl, etc.).

$$Mn(OAc)_3 + 2HBr \rightarrow 2HOAc + Mn(OAc)Br_2 \rightarrow Mn(OAc)_2 + HBr_2. \quad (6)$$

Comparative examples 5g and 5h show the inhibiting effect of excess manganese. Therefore it is desirable to limit the amount of manganese, during the oxidation process, to achieve high yield of FDCA.

It is very important to note that in a continuous process under the same conditions as described in this invention report (conducted as a batch process) higher than 90% yield of FDCA expected due to efficient supply of oxygen and mixing.

TABLE 5

Results from semi-batch reactions performed as described above.*

| Example | Bromide source | Co conc (ppm) | Mn conc (ppm) | Br conc (ppm) | yield of FDCA (%) | yield of FFCA (%) | CO (total mol) | CO$_2$ (total mol) | CO$_x$ (mol/min) | pH, before reaction | Color (b*) |
|---|---|---|---|---|---|---|---|---|---|---|---|
| 5a | solid NaBr | 2000 | 93.3 | 3000 | 81.6 | 0.81 | 0.013 | 0.078 | 0.000758 | −0.12 | 13.91 |
| 5b | solid NaBr | 2000 | 93.3 | 3000 | 82.6 | 0.87 | 0.013 | 0.092 | 0.000875 | −0.12 | 14.14 |
| 5c | aqueous HBr | 2000 | 93.3 | 3000 | 89.4 | 0.58 | 0.003 | 0.061 | 0.000533 | −1.03 | 5.845 |
| 5d | aqueous HBr | 2000 | 93.3 | 3000 | 88.6 | 0.8 | 0.0037 | 0.061 | 0.000539 | −1.03 | 6.175 |
| 5e | aqueous HBr + solid NaBr | 2000 | 93.3 | 3000 | 91.7 | 0.96 | 0.008 | 0.07 | 0.000650 | −0.63 | 8.185 |
| 5f | aqueous HBr + solid NaBr | 2000 | 93.3 | 3000 | 90.2 | 0.87 | 0.008 | 0.072 | 0.000667 | −0.63 | 7.95 |
| 5g | aqueous HBr | 2000 | 2000 | 3000 | 79.4 | 1.08 | 0.009 | 0.072 | 0.000675 | −0.84 | 6.21 |
| 5h | aqueous HBr | 2000 | 2000 | 3000 | 80.5 | 1.32 | 0.009 | 0.071 | 0.000667 | −0.84 | 6.31 |

*T = 132 C., P = 130 psig. CO$_x$ (mol/min) = CO (mol/min) + CO$_2$ (mol/min). FFCA = 5-Formylfuran-2-carboxylic acid.

9) Disassemble the die and remove the cup. Place the cup into a labeled plastic bag (Nasco Whirl-Pak 4 oz).
10) Using a HunterLab Colorquest XE colorimeter, create the following method (Hunterlab EasyQuest QC software, version 3.6.2 or later)
Mode: RSIN-LAV (Reflectance Specular Included-Large Area View)
Measurements:
CIE L* a* b*
CIE X Y Z
11) Standardize the instrument as prompted by the software using the light trap accessory and the certified white tile accessory pressed against the reflectance port.
12) Run a green tile standard using the certified white tile and compare the CIE X, Y, and Z values obtained against the certified values of the tile. The values obtained should be ±0.15 units on each scale of the stated values.
13) Analyze the sample in the bag by pressing it against the reflectance port and obtaining the spectrum and L*, a*, b* values. Obtain duplicate readings and average the values for the report.
Interpretation of Results:
Examples 5c, 5d, 5e and 5f (Table-5) which use catalyst systems consisting of cobalt, manganese and aqueous hydrobromic acid or aqueous hydrobromic acid and sodium bromide as a bromide source produced about 90% yield of FDCA, minimum colored impurities (measured by b*) and a minimum level of CO and CO$_2$ (CO$_x$ mol/min) in the off-gas. One of the reasons for the differences in activity between hydrobromide and sodium bromide, in a single batch reaction, is due to faster oxidation of HBr by Mn(III), eq 6, than sodium bromide (it is about 22 times faster: Jiao, X. J.; Espe- Example Set 4

Figure 2:
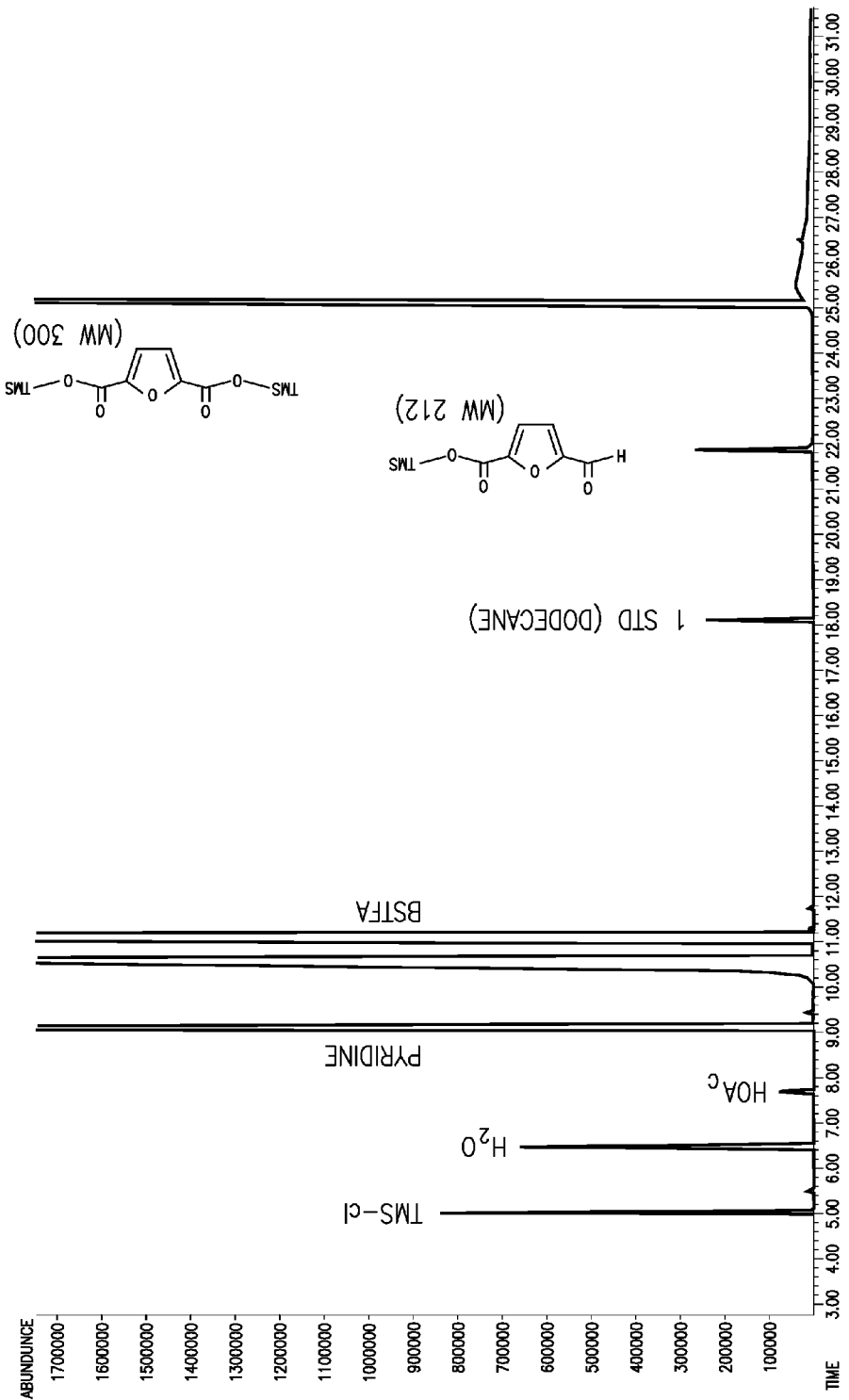
FIG. 2 illustrates an embodiment of the invention, showing the GC chromatogram of the carboxylic acid composition 110 that has been dried.
Figure 3:
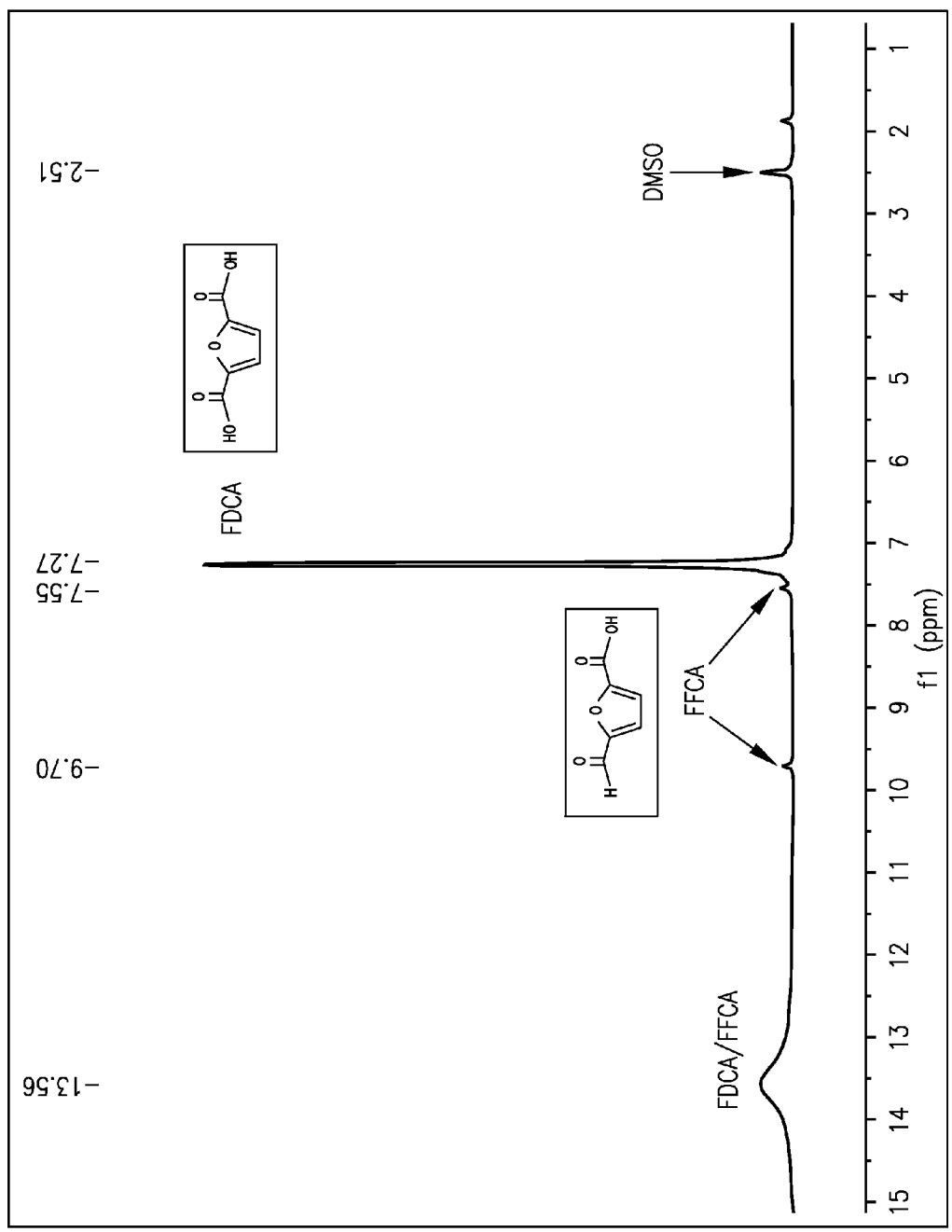
FIG. 3 illustrates an embodiment of the invention, showing a $^1$H NMR of the carboxylic acid composition 110 that has been dried.
Figure 4:
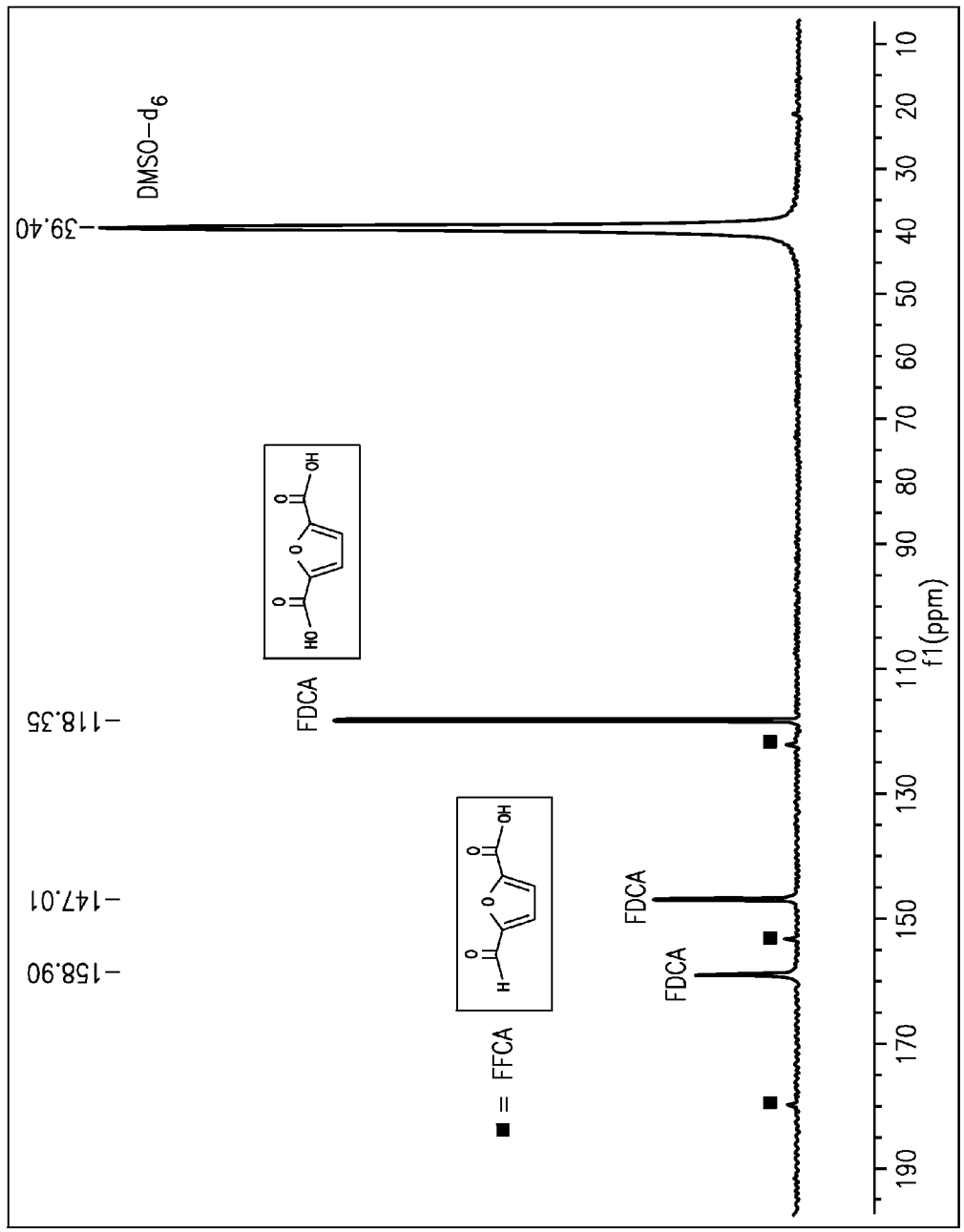
FIG. 4 illustrates an embodiment of the invention, showing a $^{13}$C{$^1$H} NMR of the carboxylic acid composition 110 that has been dried.

In Examples 1-34, 72, 73, 85, 86, 91, 92 and 93 glacial acetic acid and the catalyst components in concentrations described in the Tables 6 and 7 were transferred to a 300 mL titanium autoclave equipped with a high pressure condenser, a baffle and an Isco pump. Cobalt, manganese and ionic bromine were provided as cobalt (II) acetate tetrahydrate, manganese (II) acetate and sodium bromide/aqueous hydrobromic acid respectively. The autoclave was pressurized with approximately 50 psig of nitrogen and then the homogeneous mixture was heated to the desired temperature in a closed system (i.e., with no gas flow) with stirring. At reaction temperature, an air flow of 1500 sccm was introduced at the bottom of the solution and the reaction pressure was adjusted to the desired pressure. A solution of 5-HMF in acetic acid was fed to the mixture at a rate of 0.833 mL/min via a high pressure Isco pump (this is t=0 for the reaction time). After 30 seconds from the start of 5-HMF feeding, 1.0 g of peracetic acid in 5.0 mL of acetic acid was introduced using a blowcase to start the reaction. The feed was stopped after 1 h and the reaction continued for 1 more hour at the same conditions of air flow, temperature and pressure. After the reaction time was completed the air flow was stopped and the autoclave was cooled to room temperature and depressurized. The heterogeneous mixture was filtered to isolate the crude FDCA. The mass of the filtrate was recorded. The crude FDCA was washed with 60 mL of acetic acid two times and then twice with 100 mL of DI water. The washed crude FDCA was oven dried at 110° C. under vacuum overnight and then weighed. The solid and the filtrate were analyzed by Gas Chromatography using BSTFA derivatization method. A typical GCchromatogram for isolated crude FDCA sample is shown in FIG. 2. The purity of this solid was confirmed by NMR spectroscopy, FIGS. 3 and 4.

The Off-gas was analyzed for CO and $CO_2$ by ND-1R (ABB, Advanced Optima) and $O_2$ by a paramagnetism detection system (Servomex, 1440 Model).

Analytical

Gas Chromatographic Method Process sample was analyzed using a Shimadzu gas chromatograph Model 2010 (or equivalent) equipped with a split/heated injector (300° C.) and a flame ionization detector (300° C.). A capillary column (60 meter×0.32 mm ID) coated with (6% cyanopropylphenyl)-methylpolysiloxane at 1.0 μm film thickness (such as DB-1301 or equivalent) was employed. Helium was used as the carrier gas with an initial column head pressure of 29.5 psi and an initial column flow of 3.93 ml/minute while the carrier gas linear velocity of 45 cm/second was maintained constant throughout the entire oven temperature program. The column temperature was programmed as follows: The initial oven temperature was set at 80° C. and was held for 6 minutes, the oven was ramped up to 150° C. at 4° C./minute and was held at 150 for 0 minute, the oven was ramped up to 240° C. at 10° C./minute and was held at 240 for 5 minute, then the oven was ramped up to 290° C. at 10° C./minute and was held at 290 for 17.5 minutes (the total run time was 60 mins). 1.0-μl of the prepared sample solution was injected with a split ratio of 40:1. EZ-Chrom Elite chromatography data system software was used for data acquisition and data processing. The sample preparation was done by weighing 0.1 g (accurate to 0.1 mg) of sample in a GC vial and adding 200.0 μl ISTD solution (1% by volume of decane in pyridine) and 1000 μl of BSTFA (N,O-bis(trimethylsilyl)trifluoroacetamide) with 1% TMSCl (trimethylchlorosilane) to the GC vial. The content was heated at 80° C. for 30 minutes to ensure complete derivatization. 1.0-μl of this prepared sample solution was injected for GC analysis.

Interpretation of Results:

Experiments 1-34, Table 6, were conducted by varying temperature, pressure and levels of cobalt and bromine concentrations to determine optimum conditions and catalyst compositions that produces very high yield of FDCA with minimum amount of carbon burn. In this invention, the weight ratio of cobalt to manganese was deliberately kept very high (i.e. 21) in all the reactions to avoid the inhibiting effect of excess manganese especially below 160° C.

Figure 5:
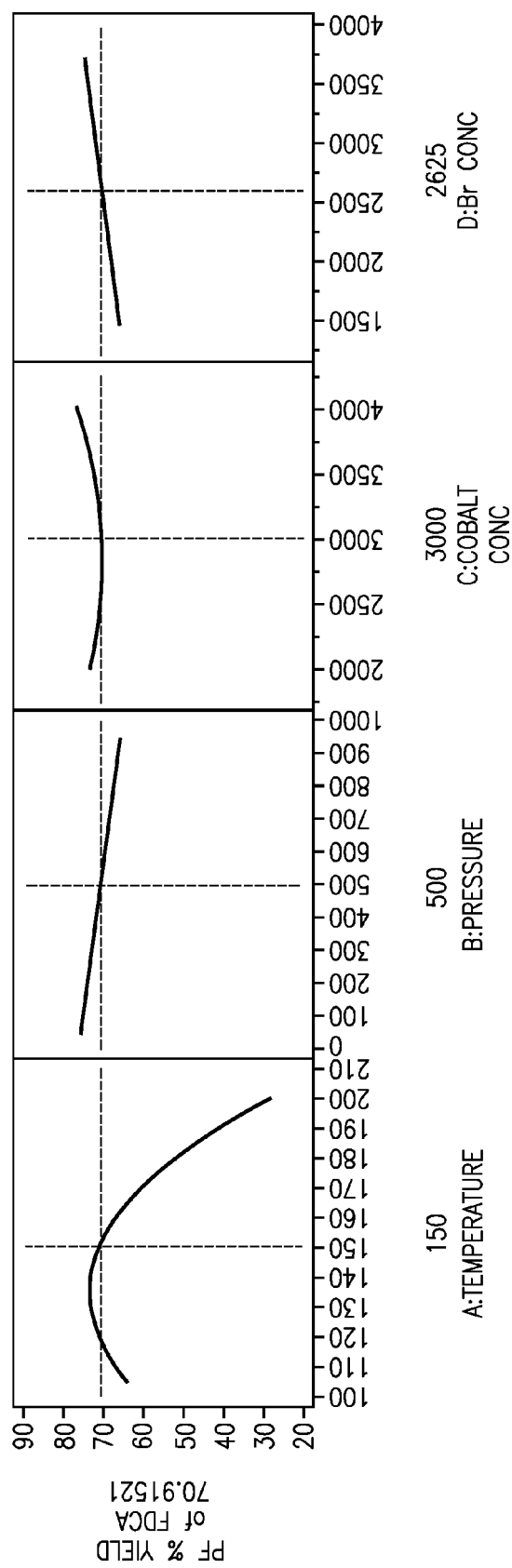
FIG. 5 illustrates an embodiment of the invention, showing the effects of temperature, pressure, cobalt and bromine concentrations have on the FDCA yield in the carboxylic acid composition 110.

As can be seen from FIG. 5, under the reaction conditions investigated in this invention the factor that has the most impact on the yield of FDCA is temperature. It is also important to note that the yield increases with increasing cobalt and bromine concentrations.

The data presented in Table 6 was used to develop a theoretical polynomial model to predict FDCA yield under different conditions, eq-7. Examples of predicted FDCA yields using this model is given in Table 7. Experiments No 72, 73, 85, and 86, Table 7, were conducted under the predicted conditions. As can be seen from the results they agree well with the predicted values within experimental error.

$$\% \text{ yield of FDCA} = -91.469 + 2.83*T - 0.01*P - 0.02*[Co] + 0.003*[Br] - 0.01*T^2 + 3.9*10^{-6}*[Co]^2 \quad (7)$$

Examples 91-93, Table 8, were conducted under the US patent applications (US2003/0055271 A1) conditions using our set-up. As can be seen from Tables 6, 7 and 8, the patent application conditions gave much inferior yield of FDCA than the current invention.

TABLE 6

Results from semi-batch reactions performed as described above.*

| Run | A: Temperature deg, C. | B: Pressure psi | C: Cobalt conc ppm | D: Br conc ppm | % conversion | % yield of FDCA | % yield of FFCA | CO (total mol) | CO2 (total mol) | $CO_x$ (mol/min) |
|---|---|---|---|---|---|---|---|---|---|---|
| 1 | 130 | 200 | 4000 | 1500 | 99.26 | 75.7 | 1.1 | 0.011 | 0.088 | 0.00083 |
| 2 | 155 | 450 | 3000 | 2250 | 99.1 | 67.3 | 0.08 | 0.032 | 0.163 | 0.00163 |
| 3 | 180 | 200 | 4000 | 3000 | 100 | 68.7 | 0.037 | 0.049 | 0.161 | 0.00175 |
| 4 | 180 | 700 | 2000 | 3000 | 98.57 | 57.3 | 0.0049 | 0.044 | 0.17 | 0.00178 |
| 5 | 180 | 200 | 2000 | 1500 | 94.47 | 48.3 | 0.96 | 0.044 | 0.125 | 0.00141 |
| 6 | 155 | 450 | 3000 | 2250 | 99.07 | 67.2 | 0.07 | 0.031 | 0.158 | 0.00158 |
| 7 | 130 | 700 | 4000 | 3000 | 100 | 78 | 0.34 | 0.017 | 0.183 | 0.00167 |
| 8 | 130 | 200 | 2000 | 3000 | 97.11 | 82.1 | 1.1 | 0.012 | 0.095 | 0.00089 |
| 9 | 180 | 700 | 4000 | 1500 | 99.5 | 53 | 0.02 | 0.053 | 0.148 | 0.00168 |
| 10 | 155 | 450 | 3000 | 2250 | 99.38 | 70.9 | 0.148 | 0.032 | 0.16 | 0.00160 |
| 11 | 130 | 700 | 2000 | 1500 | 99.84 | 68 | 0.79 | 0.024 | 0.168 | 0.00160 |
| 12 | 180 | 200 | 4000 | 1500 | 99.26 | 53.3 | 0.003 | 0.061 | 0.185 | 0.00205 |
| 13 | 155 | 450 | 3000 | 2250 | 100 | 70 | 0.2 | 0.03 | 0.158 | 0.00157 |
| 14 | 130 | 200 | 2000 | 1500 | 96.2 | 74.6 | 1.49 | 0.015 | 0.093 | 0.00090 |
| 15 | 130 | 200 | 4000 | 3000 | 99.57 | 85.3 | 0.7 | 0.009 | 0.083 | 0.00077 |
| 16 | 130 | 700 | 4000 | 1500 | 99.9 | 73.9 | 0.87 | 0.018 | 0.129 | 0.00123 |
| 17 | 155 | 450 | 3000 | 2250 | 100 | 71.2 | 0.1 | 0.03 | 0.159 | 0.00158 |
| 18 | 130 | 700 | 2000 | 3000 | 99.89 | 70.3 | 0.54 | 0.02 | 0.13 | 0.00125 |
| 19 | 180 | 200 | 2000 | 3000 | 99.5 | 58.4 | 0.464 | 0.058 | 0.0193 | 0.00064 |
| 20 | 180 | 700 | 2000 | 1500 | 100 | 54.3 | 0.55 | 0.053 | 0.175 | 0.00190 |
| 21 | 155 | 450 | 3000 | 2250 | 100 | 58.5 | 0.089 | 0.029 | 0.155 | 0.00153 |
| 22 | 180 | 700 | 4000 | 3000 | 100 | 60 | 0.025 | 0.048 | 0.158 | 0.00172 |
| 23 | 200 | 450 | 3000 | 2250 | 100 | 23 | 0 | 0.158 | 0.284 | 0.00368 |
| 24 | 200 | 450 | 3000 | 2250 | 100 | 23.8 | 0 | 0.156 | 0.266 | 0.00352 |
| 25 | 155 | 450 | 3000 | 2250 | 99.69 | 66.2 | 0.143 | 0.028 | 0.154 | 0.00152 |
| 26 | 155 | 50 | 3000 | 2250 | 99.05 | 79 | 0.075 | 0.019 | 0.109 | 0.00107 |
| 27 | 155 | 450 | 3000 | 1500 | 98.14 | 67.4 | 0.18 | 0.032 | 0.15 | 0.00152 |
| 28 | 155 | 950 | 3000 | 2250 | 99.94 | 62.8 | 0.118 | 0.034 | 0.164 | 0.00165 |
| 29 | 155 | 450 | 3000 | 2250 | 99.81 | 68.9 | 0.093 | 0.027 | 0.152 | 0.00149 |
| 30 | 105 | 450 | 3000 | 2250 | 97.12 | 66.9 | 3.56 | 0.013 | 0.099 | 0.00093 |
| 31 | 155 | 450 | 4000 | 2250 | 99.92 | 66.4 | 0.06 | 0.032 | 0.158 | 0.00158 |
| 32 | 155 | 450 | 3000 | 3750 | 100 | 68.8 | 0.178 | 0.026 | 0.151 | 0.00148 |

TABLE 6-continued

Results from semi-batch reactions performed as described above.*

| Run | A: Temperature deg, C. | B: Pressure psi | C: Cobalt conc ppm | D: Br conc ppm | % conversion | % yield of FDCA | % yield of FFCA | CO (total mol) | CO2 (total mol) | CO$_x$ (mol/min) |
|---|---|---|---|---|---|---|---|---|---|---|
| 33 | 155 | 450 | 3000 | 2250 | 99.76 | 72 | 0.1 | 0.027 | 0.154 | 0.00151 |
| 34 | 155 | 450 | 2000 | 2250 | 99.89 | 70.3 | 0.54 | 0.02 | 0.13 | 0.00125 |

*Cobalt to manganese weight ratio = 21 for all experiments

TABLE 7

Predicted yields of FDCA. 72, 73, 74, 85 and 86 are experimental results.*

| No. | Temp. | Pressure | Cobalt conc | Br conc | Yield of FDCA | Yield of FFCA |
|---|---|---|---|---|---|---|
| 35 | 139 | 50 | 3999 | 3000 | 85.1504 | 0.447749 |
| 36 | 139 | 50 | 4000 | 2981 | 85.0945 | 0.442835 |
| 37 | 138 | 70 | 4000 | 3000 | 85.0502 | 0.469564 |
| 38 | 138 | 74 | 4000 | 3000 | 85.0244 | 0.473723 |
| 39 | 138 | 63 | 3988 | 3000 | 84.9913 | 0.463436 |
| 40 | 139 | 50 | 3999 | 2948 | 84.976 | 0.435265 |
| 41 | 139 | 50 | 4000 | 2938 | 84.9472 | 0.432597 |
| 42 | 139 | 50 | 3981 | 2973 | 84.9129 | 0.443582 |
| 43 | 138 | 51 | 3951 | 2999 | 84.7494 | 0.455411 |
| 44 | 138 | 50 | 3935 | 2999 | 84.629 | 0.455856 |
| 45 | 138 | 50 | 3917 | 3000 | 84.4874 | 0.458526 |
| 46 | 138 | 53 | 3917 | 3000 | 84.4716 | 0.461423 |
| 47 | 138 | 50 | 4000 | 2777 | 84.3976 | 0.406641 |
| 48 | 138 | 50 | 3905 | 2998 | 84.3893 | 0.45981 |
| 49 | 137 | 50 | 3881 | 3000 | 84.2031 | 0.463274 |
| 50 | 139 | 50 | 3886 | 3000 | 84.1187 | 0.428238 |
| 51 | 137 | 50 | 4000 | 2596 | 83.7624 | 0.395897 |
| 52 | 137 | 50 | 3992 | 2606 | 83.724 | 0.39788 |
| 53 | 136 | 50 | 3804 | 3000 | 83.6075 | 0.473555 |
| 54 | 136 | 51 | 3780 | 3000 | 83.4262 | 0.477259 |
| 55 | 137 | 227 | 3994 | 3000 | 83.3911 | 0.433817 |
| 56 | 137 | 50 | 4000 | 2386 | 82.9936 | 0.394841 |
| 57 | 135 | 50 | 3694 | 2946 | 82.6042 | 0.479136 |
| 58 | 135 | 50 | 4000 | 2166 | 82.2022 | 0.446345 |
| 59 | 136 | 50 | 4000 | 2152 | 82.1354 | 0.433632 |
| 60 | 131 | 61 | 2000 | 3000 | 81.8774 | 1.49331 |
| 61 | 131 | 59 | 2002 | 2993 | 81.8506 | 1.4836 |
| 62 | 131 | 59 | 2000 | 2986 | 81.8418 | 1.48296 |
| 63 | 131 | 55 | 2026 | 3000 | 81.7822 | 1.4441 |
| 64 | 130 | 83 | 2000 | 3000 | 81.5573 | 1.48713 |
| 65 | 132 | 50 | 2074 | 3000 | 81.5533 | 1.34737 |
| 66 | 130 | 91 | 2000 | 3000 | 81.7403 | 1.47787 |
| 67 | 130 | 89 | 2000 | 3000 | 81.4632 | 1.4882 |
| 68 | 132 | 50 | 2103 | 3000 | 81.3982 | 1.28915 |
| 69 | 131 | 50 | 2005 | 2833 | 81.2848 | 1.37298 |
| 70 | 139 | 51 | 4000 | 1973 | 81.2207 | 0.327309 |
| 71 | 132 | 130 | 2000 | 3000 | 81.1875 | 1.33938 |
| 72 Experimental result* | 132 | 130 | 2000 | 3000 | 81.5 | 0.79 |
| 73 Experimental result* | 132 | 130 | 2000 | 3000 | 81.6 | 0.81 |
| 74 Experimental result* | 132 | 130 | 2000 | 3000 | 81.6 | 0.81 |
| 75 | 132 | 50 | 2144 | 3000 | 81.1813 | 1.21129 |
| 76 | 131 | 50 | 2146 | 2993 | 81.1115 | 1.22154 |
| 77 | 132 | 50 | 2160 | 3000 | 81.1035 | 1.18214 |
| 78 | 132 | 50 | 2001 | 2739 | 81.0004 | 1.30911 |
| 79 | 132 | 50 | 2000 | 2681 | 80.7904 | 1.28011 |
| 80 | 133 | 50 | 2228 | 2993 | 80.7581 | 1.06473 |
| 81 | 133 | 52 | 2000 | 2563 | 80.3266 | 1.22742 |
| 82 | 133 | 50 | 2000 | 2484 | 80.0491 | 1.2075 |
| 83 | 130 | 51 | 3136 | 3000 | 79.8341 | 0.591352 |
| 84 | 133 | 50 | 4000 | 1542 | 79.8127 | 0.750216 |
| 85 | 135 | 50 | 3066 | 3000 | 79.7967 | 0.503153 |
| 85 | 135 | 50 | 3066 | 3000 | 85.3 | 0.86 |

TABLE 7-continued

Predicted yields of FDCA. 72, 73, 74, 85 and 86 are experimental results.*

| No. | Temp. | Pressure | Cobalt conc | Br conc | Yield of FDCA | Yield of FFCA |
|---|---|---|---|---|---|---|
| Experimental result* 86 | 135 | 50 | 3066 | 3000 | 83.2 | 0.96 |
| Experimental result* 87 | 134 | 50 | 4000 | 1527 | 79.7531 | 0.668935 |
| 88 | 135 | 206 | 2262 | 3000 | 78.9815 | 0.792438 |
| 89 | 132 | 50 | 2000 | 2052 | 78.3528 | 1.25619 |
| 90 | 137 | 627 | 2000 | 3000 | 75.8366 | 0.489432 |

*Cobalt to Manganese weight ratio = 21 for all experiments.

TABLE 8

Reactions conducted using the patent application (US20030055271A1) conditions.[a]

| Run | A: Temp. | B: Pressure | C: Cobalt conc | D: Br conc | % conversion | % yield of FDCA | % yield of FFCA | CO (total mol) | CO2 (total mol) | $CO_x$ (mol/min) |
|---|---|---|---|---|---|---|---|---|---|---|
| Patent US2003/0055271A1 | 125 | 950 | 406 | 1102 | | 44.7 | 2.4 | | | |
| 91[b] | 125 | 950 | 406 | 1102 | 98.42 | 40.1 | 2.3 | 0.03 | 0.128 | 0.00132 |
| Patent US2003/0055271A1 | 100 | 950 | 406 | 1102 | | 44.8 | 3.3 | | | |
| 92[B] | 100 | 950 | 406 | 1102 | 60.51 | 0.5 | 4.4 | 0.005 | 0.028 | 0.00028 |
| 93[B] | 100 | 950 | 406 | 1102 | 64.33 | 0.9 | 2.7 | 0.005 | 0.031 | 0.00030 |

[a]Cobalt to Manganese ratio = 1.
[b]Unknown peaks in the GC.

Examples Set 5

In Examples 9a-11b, glacial acetic acid and the catalyst components in concentrations described in Tables 9, 10 and 11 were transferred to a 300 mL titanium autoclave equipped with a high pressure condenser, a baffle and an Isco pump. Cobalt, manganese and ionic bromine were provided as cobalt (II) acetate tetrahydrate, manganese (II) acetate and aqueous hydrobromic acid respectively. The autoclave was pressurized with approximately 50 psig of nitrogen and the homogeneous mixture was heated to the desired temperature in a closed system (i.e., with no gas flow) with stirring. At reaction temperature, an air flow of 1500 sccm was introduced at the bottom of the solution and the reaction pressure was adjusted to the desired pressure. A solution of 5-MF/5-AMF/5-EMF in acetic acid was fed to the mixture at a rate of 0.833 mL/min via a high pressure Isco pump (this is t=0 for the reaction time). After 30 seconds from the start of substrate feeding, 1.0 g of peracetic acid in 5.0 mL of acetic acid was introduced using a blow-case to start the reaction. The feed was stopped after 1 h and the reaction continued for an additional hour at the same conditions of air flow, temperature and pressure. After the reaction time was completed, the air flow was stopped and the autoclave was cooled to room temperature and depressurized. The heterogeneous mixture was filtered to isolate the crude FDCA. The mass of the filtrate was recorded. The crude FDCA was washed with 60 mL of acetic acid two times and then twice with 100 mL of DI water. The washed crude FDCA was oven dried at 110° C. under vacuum overnight and then weighed. The solid and the filtrate were analyzed by Gas Chromatography using BSTFA derivatization method.

The off-gas was analyzed for CO and $CO_2$ by ND-1R (ABB, Advanced Optima) and $O_2$ by a paramagnetism detection system (Servomex, 1440 Model).

Analytical

Gas Chromatographic Method Process samples were analyzed using a Shimadzu gas chromatograph Model 2010 (or equivalent) equipped with a split/heated injector (300° C.) and a flame ionization detector (300° C.). A capillary column (60 meter×0.32 mm ID) coated with (6% cyanopropylphenyl)-methylpolysiloxane at 1.0 μm film thickness (such as DB-1301 or equivalent) was employed. Helium was used as the carrier gas with an initial column head pressure of 29.5 psi and an initial column flow of 3.93 mL/minute while the carrier gas linear velocity of 45 cm/second was maintained constant throughout the entire oven temperature program. The column temperature was programmed as follows: The initial oven temperature was set at 80° C. and was held for 6 minutes, the oven was ramped up to 150° C. at 4° C./minute and was held at 150° C. for 0 minute, the oven was ramped up to 240° C. at 10° C./minute and was held at 240° C. for 5 minutes, then the oven was ramped up to 290° C. at 10° C./minute and was held at 290° C. for 17.5 minutes (the total run time was 60 mins). 1.0-μl of the prepared sample solution was injected with a split ratio of 40:1. EZ-Chrom Elite chromatography data system software was used for data acquisition and data processing. The sample preparation was done by weighing 0.1 g (accurate to 0.1 mg) of sample in a GC vial and adding 200.0 μl ISTD solution (1% by volume of decane in pyridine) and 1000 μl of BSTFA (N,O-bis(trimethylsilyl)trifluoroacetamide) with 1% TMSCl (trimethylchlorosilane) to the GC vial. The content was heated at 80° C. for 30 minutes to ensure complete derivatization. 1.0-μl of this prepared sample solution was injected for GC analysis.

Interpretation of Results:

5-AMF Feed Studies:

Oxidation of 5-AMF, which contains an oxidizable ester and aldehydes moieties, produced FDCA, FFCA, and acetic acid, eq 8. Experiments 9a-9k, Table 9, were conducted by varying temperature, and levels of cobalt and bromine concentrations to determine optimum conditions and catalyst compositions that produces very high yield of FDCA with minimum amount of carbon burn. In this invention, the weight ratio of cobalt to manganese was deliberately kept very high (i.e. 21) in all the reactions to avoid the inhibiting effect of excess manganese especially below 160° C. Further discussion on mechanism of initiation and inhibition by Mn(II) in oxidation can be found in Zakharov, I. V. *Kinetics and Catalysis* 1998, 39, 485; and Jiao, X. J.; Espenson, J. H. *Inorg. Chem.* 2000, 39, 1549.

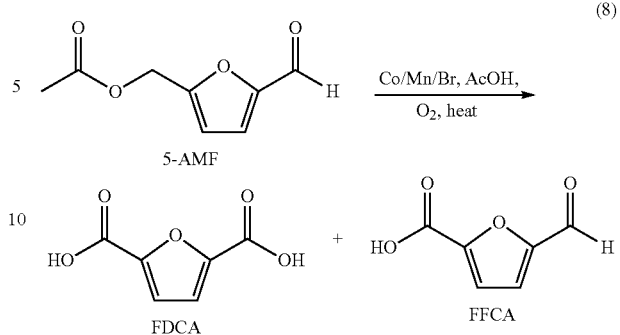

(8)

TABLE 9

Results from semi-batch reactions performed as described above using 5-AMF feed.*

| Run | Factor 1 Temperature (° C.) | Factor 2 Pressure (psig) | Factor 3 Cobalt conc (ppmw) | Factor 4 Br conc (ppmw) | Response 1 % yield of FDCA | Response 2 % yield of FFCA |
|---|---|---|---|---|---|---|
| 9a | 180 | 130 | 2500 | 2500 | 44.6 | 0.25 |
| 9b | 130 | 130 | 2500 | 2500 | 88.2 | 0.25 |
| 9c | 155 | 130 | 2000 | 3000 | 67.6 | 0.026 |
| 9d | 130 | 130 | 2000 | 3000 | 90.2 | 0.16 |
| 9e | 155 | 130 | 2500 | 2500 | 64.52 | 0.35 |
| 9f | 180 | 130 | 2000 | 3000 | 49.5 | 0.15 |
| 9g | 105 | 130 | 2000 | 3000 | 64.8 | 1.8 |
| 9h | 180 | 130 | 2000 | 3000 | 42.3 | 0.007 |
| 9i | 180 | 130 | 2500 | 2500 | 40.9 | 0.06 |
| 9j | 130 | 130 | 2000 | 3000 | 86.9 | 0.79 |
| 9k | 130 | 130 | 2500 | 2500 | 88.5 | 0.71 |

*Cobalt to Manganese weight ratio = 21 for all experiments

Figure 6:
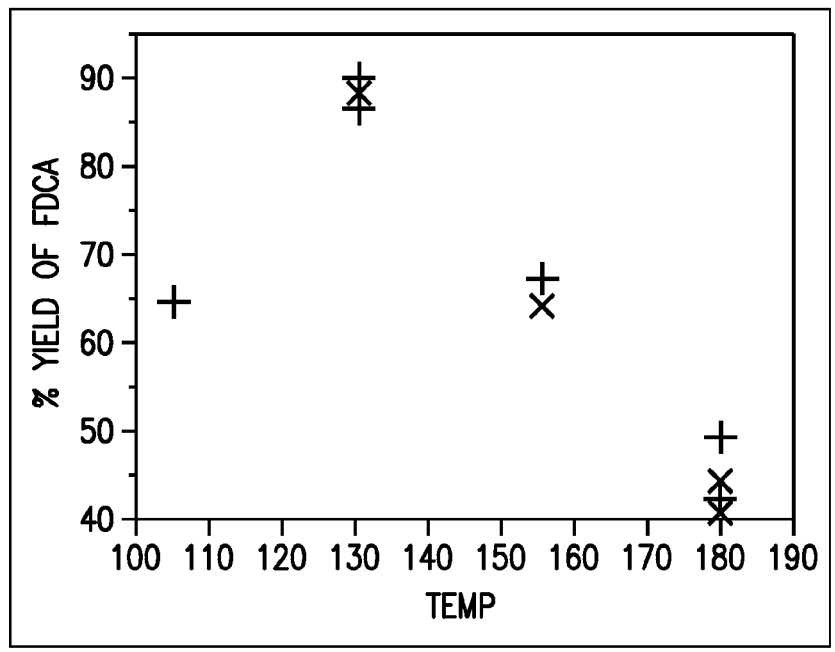
FIG. 6 illustrates an embodiment of the invention, Effect of temperature on yield using an oxidizable raw material stream 30 comprising 5-AMF. The + symbol represents that Co is 2000 ppm and Br is 3000 ppm. The × symbol represents that Co is 2500 ppm and Br is 2500 ppm.

As can be seen from FIG. 6, under the reaction conditions investigated, in this invention, the factor that has the most impact on the yield of FDCA is temperature. It is also important to note that the yield can increase with increasing cobalt and bromine concentrations.

It is important to note that the same yield and selectivity can be obtained with mixed 5-HMF and 5-AMF feed-stocks with varying ratios of the two components.

5-EMF Feed Study:

Oxidation of 5-EMF, which contains an oxidizable ether and aldehyde moieties, produced FDCA, FFCA, 5-(ethoxycarbonyl)furan-2-carboxylic acid (EFCA) and acetic acid, eq 9.

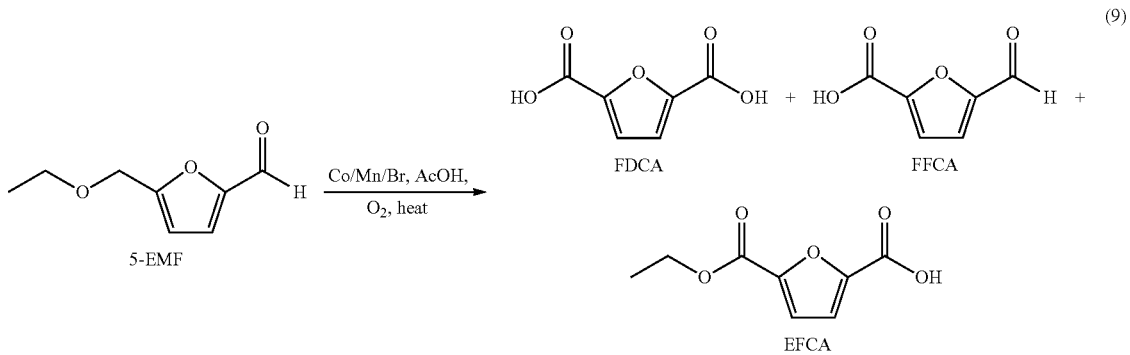

(9)

Experiments 10a-10k, Table 10, were conducted by varying temperature, and levels of cobalt and bromine concentrations to determine optimum conditions and catalyst compositions that produces very high yield of FDCA with minimum amount of carbon burn. Similar to the 5-AMF oxidation described above the weight ratio of cobalt to manganese was deliberately kept very high (i.e. 21) in all the reactions to avoid the inhibiting effect of excess manganese especially below 160° C.

TABLE 10

Results from semi-batch reactions performed as described above using 5-EMF feed.*

| Run | Factor 1 Temperature (° C.) | Factor 2 Pressure (psig) | Factor 3 Cobalt conc (ppmw) | Factor 4 Br conc (ppmw) | Response 1 % yield of FDCA | Response 2 % yield of FFCA | Response 3 % yield of EFCA |
|---|---|---|---|---|---|---|---|
| 10a | 180 | 130 | 2500 | 2500 | 52.3 | 0.031 | 0.117 |
| 10b | 130 | 130 | 2500 | 2500 | 88.8 | 0.02 | 0.225 |
| 10c | 155 | 130 | 2000 | 3000 | 57.5 | 0.058 | 0.28 |
| 10d | 130 | 130 | 2000 | 3000 | 87.97 | 0.09 | 0.43 |
| 10e | 155 | 130 | 2500 | 2500 | 64.52 | 0.35 | 0.47 |
| 10f | 180 | 130 | 2000 | 3000 | 49.5 | 0.15 | 0.23 |
| 10g | 105 | 130 | 2000 | 3000 | 86 | 2.92 | 1.4 |
| 10h | 180 | 130 | 2000 | 3000 | 50.9 | 0.096 | 0.24 |
| 10i | 180 | 130 | 2500 | 2500 | 48.9 | 0.4 | 0.61 |
| 10j | 130 | 130 | 2000 | 3000 | 87.5 | 0.4 | 1.22 |
| 10k | 130 | 130 | 2500 | 2500 | 87.4 | 0.42 | 1.3 |

*Cobalt to Manganese weight ratio = 21 for all experiments

Figure 7:
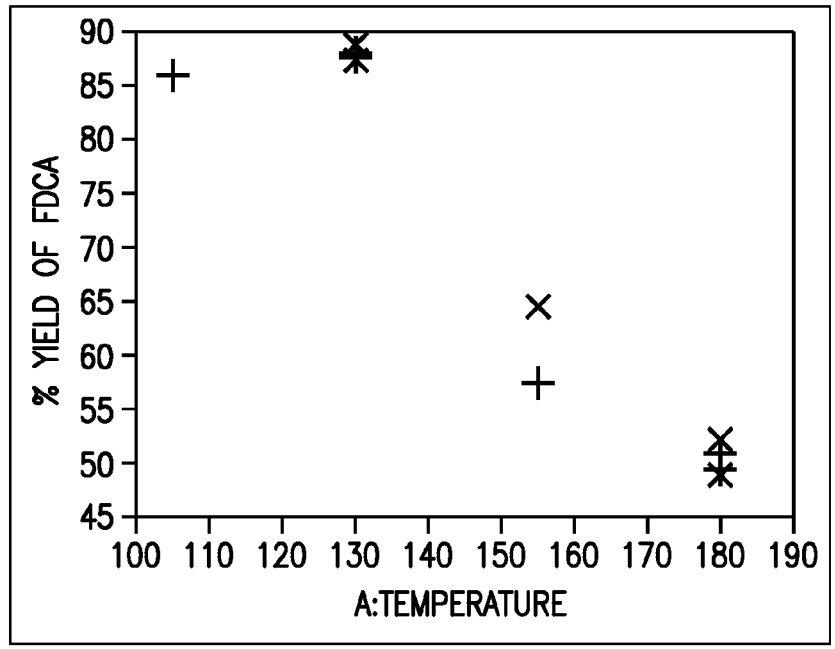
FIG. 7 illustrates an embodiment of the invention, Effect of temperature on yield using an oxidizable raw material stream 30 comprising 5-EMF. The + symbol represents that Co is 2000 ppm and Br is 3000 ppm. The × symbol represents that Co is 2500 ppm and Br is 2500 ppm.

As can be seen from FIG. 7, under the reaction conditions investigated in this invention the factor that has the most impact on the yield of FDCA is temperature. It is important to note that the same yield and selectivity can be obtained with mixed 5-HMF and 5-EMF feed-stocks with varying ratios of the two components.

5-MF Feed Study:

Oxidation of 5-MF, which contains an oxidizable methyl and aldehydesmoieties, produced FDCA, and FFCA eq 10. Experiments 11a and 11b, Table 11, demonstrate that moderate yield of FDCA with high purity can be obtained using 5-MF as a feed stock.

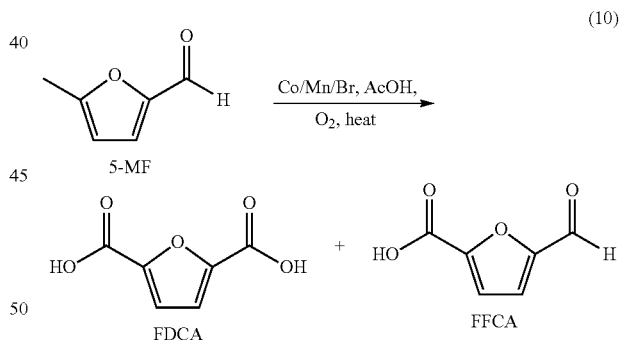

(10)

TABLE 11

Results from semi-batch reactions performed as described above using 5-MF feed.*

| Run | Factor 1 Temperature (° C.) | Factor 2 Pressure (psig) psi | Factor 3 Cobalt conc (ppmw) ppm | Factor 4 Br conc (ppmw) ppm | Response 1 % conversion | Response 2 % yield of FDCA | Response 3 % yield of FFCA |
|---|---|---|---|---|---|---|---|
| 11a | 130 | 130 | 2000 | 3000 | 100 | 61.3 | 0.082 |
| 11b | 130 | 400 | 2500 | 2500 | 100 | 61.8 | 0.083 |

*Cobalt to Manganese weight ratio = 21.

It is very important to note that in a continuous process under the same conditions as described in this invention report (which was conducted as a batch process) with different feed stock even higher yields of crude FDCA is expected due to efficient mixing, relatively low concentrations of reactive intermediates, and other reasons familiar to those skilled in the art.

Claims Not Limited to Disclosed Embodiments

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

We claim:

1. A carboxylic acid composition comprising:
   (a) furan-2,5-dicarboxylic acid in an amount greater than 90 weight percent;
   (b) a b* value of less than 15; and
   (c) 5-formyl furan-2-carboxylic acid (FFCA) in a range of from about 0.1 to about 4.0 weight percent.

2. A carboxylic acid composition according to claim 1 where said furan-2,5-dicarboxylic acid is in an amount greater than 92 weight percent.

3. A carboxylic acid composition according to claim 2 wherein said carboxylic acid composition has a b* value of less than 10.

4. A carboxylic acid composition according to claim 2 wherein said carboxylic acid composition has a b* value of less than 5.

5. A carboxylic acid composition according to claim 1 where said furan-2,5-dicarboxylic acid is in an amount greater than 94 weight percent.

6. A carboxylic acid composition according to claim 5 wherein said carboxylic acid composition has a b* value of less than 10.

7. A carboxylic acid composition according to claim 5 wherein said carboxylic acid composition has a b* value of less than 5.

8. A carboxylic acid composition according to claim 1 where said furan-2,5-dicarboxylic acid is in an amount greater than 96 weight percent.

9. A carboxylic acid composition according to claim 8 wherein said carboxylic acid composition has a b* value of less than 10.

10. A carboxylic acid composition according to claim 8 wherein said carboxylic acid composition has a b* value of less than 5.

11. A carboxylic acid composition according to claim 1 where said furan-2,5-dicarboxylic acid is in an amount greater than 98 weight percent.

* * * * *